US011366119B2

(12) United States Patent
Chang et al.

(10) Patent No.: US 11,366,119 B2
(45) Date of Patent: Jun. 21, 2022

(54) ENCAPSULATED FUNCTIONALIZED DIAMOND CRYSTAL

(71) Applicant: ACADEMIA SINICA, Taipei (TW)

(72) Inventors: Huan-Cheng Chang, Taipei (TW); Feng-Jen Hsieh, Kaohsiung (TW); Yen-Wei Chen, Taipei (TW)

(73) Assignee: ACADEMIA SINICA, Taipei (TW)

( * ) Notice: Subject to any disclaimer, the term of this patent is extended or adjusted under 35 U.S.C. 154(b) by 631 days.

(21) Appl. No.: 15/990,189

(22) Filed: May 25, 2018

(65) Prior Publication Data

US 2018/0340938 A1    Nov. 29, 2018

Related U.S. Application Data

(60) Provisional application No. 62/511,034, filed on May 25, 2017.

(51) Int. Cl.
*G01N 33/543* (2006.01)
*G01N 33/58* (2006.01)

(52) U.S. Cl.
CPC ......... *G01N 33/586* (2013.01); *G01N 33/582* (2013.01); *G01N 33/587* (2013.01)

(58) Field of Classification Search
CPC .. G01N 33/586; G01N 33/582; G01N 33/587; G01N 33/543; A61K 47/488
See application file for complete search history.

(56) References Cited

U.S. PATENT DOCUMENTS

| | | | | |
|---|---|---|---|---|
| 5,420,016 | A * | 5/1995 | Boguslaski | C12Q 1/04 106/2 |
| 5,536,490 | A * | 7/1996 | Klaveness | A61K 49/223 424/9.52 |
| 8,168,413 | B2 | 5/2012 | Chang et al. | |
| 10,364,389 | B1 * | 7/2019 | Shenderova | C09K 11/025 |
| 2008/0032135 | A1 * | 2/2008 | Takahashi | C09C 1/56 428/403 |
| 2009/0162425 | A1 * | 6/2009 | Divi | A61K 49/0084 424/450 |
| 2013/0164379 | A1 * | 6/2013 | Gartel | A61K 45/06 424/490 |

FOREIGN PATENT DOCUMENTS

WO    WO2016/164827 A1    10/2016

OTHER PUBLICATIONS

Hui et al., Two-photon fluorescence correlation spectroscopy of lipid-encapsulated fluorescent nanodiamonds in living cells, Optics Express, vol. 18, No. 6, Mar. 2010, pp. 5896-5905. (Year: 2010).*
Zhang et al., A Novel High Mechanical Property PLGA Composite matrix loaded with Nanodiamond-Phospholipid Compound for Bone Tissue Engineering, ACS Appl. Nater. Interfaces, Jan. 2016, vol. 8, Issue 2, pp. 1087-1097. (Year: 2016).*
Nasongkla et al., Multifunctional Polymeric Micelles as Cancer-Targeted, MRI-Ultrasensitive Drug Delivery Systems, (Nano Letters, 2006, vol. 6, No. 11, pp. 2427-2430. (Year: 2006).*
Huang et al., Active Nanodiamond Hydrogels for Chemotherapeutic Delivery, Nano Letters, 2007, vol. 7, No. 11, pp. 3305-3314. (Year: 2007).*
Nagi et al., Improving surface and defectcenterchemistry of fluorescent nanodiamonds for imaging purposes—a review, Anal Bioaanal Chem, 2015, 407, pp. 7521-7536. (Year: 2015).*
Dean, L., "Blood group antigens are surface markers on the red blood cell membrane", *Blood Groups and Red Cell Antigens*, 2005, 6 pages, Chapter 2, National Center for Biotechnology Information, Bethesda, MD, USA.
Delves, P. "CD Antigens". eLS John Wiley and Sons, 2016, 26 pages. John Wiley and Sons, Chichester, UK.
Oliver, C. and Jamur, M., "Immunocytochemical Methods and Protocols", *Methods in Molecular Biology*, 2010, 403 pages, Third Edition, Humana Press, Hatfield, UK.
Kim et al., "Quantitative analysis of the number of antigens immobilized on a glass surface by AFM", Ultramicroscopy, 2004, pp. 203-210, vol. 100.
Rica, R. and Stevens, M., "Plasmonic ELISA for the ultrasensitive detection of disease biomarkers with the naked eye", *Nature Nanotechnology*, Oct. 28, 2012, pp. 821-824. vol. 7.
Tang, D et al., "Nanoparticle-based immunoassays in the biomedical Field", *Analyst*, 2013, pp. 981-990, vol. 138.
Yu, S., et al. "Bright Fluorescent Nanodiamonds: No Photobleaching and Low Cytotoxicity" *Journal of American Chemical Society*, 2005, pp. 17604-17605, vol. 127.
Hsiao, W., "Fluorescent Nanodiamond: A Versatile Tool for Long-Term Cell Tracking, Super-Resolution Imaging, and Nanoscale Temperature Sensing", *Accounts of Chemical Research*, 2006, pp. 400-407, vol. 49.
Kuo, Y., et al.," Fluorescence lifetime imaging microscopy of nanodiamonds in vivo", *Proceedings of SPIE*, 2013, 8 pages, SPIE, San Francisco, CA, USA.
Kuo, Y., et al., "Fluorescent nanodiamond as a probe for the intercellular transport of proteins in vivo", *Biomaterials*, 2013, pp. 8352-8360, vol. 34.
Wu, T., et al., "Tracking the engraftment and regenerative capabilities of transplanted lung stem cells using fluorescent nanodiamonds", *Nature Nanotechnology*. 2013. pp. 682-689, vol. 8. Macmillan Publishers.
Sarkar, S., "Wide-field in vivo background free imaging by selective magnetic modulation of nanodiamond fluorescence", *Biomedical Optics Express*, 2014, pp. 1190-1202, vol. 5, Issue 4.
Rehor, I., et al., "Fluorescent Nanodiamonds with Bioorthogonally Reactive Protein-Resistant Polymeric Coatings", *CHEMPLUSCHEM Communications*, 2014, pp. 21-24, vol. 79.

(Continued)

*Primary Examiner* — Gary Counts
(74) *Attorney, Agent, or Firm* — Muncy, Geissler, Olds & Lowe, P.C.

(57) ABSTRACT

This invention is a functionalized diamond crystal with high dispersibility in high ionic strength solution and/or with specific targeting ability, which comprise a diamond crystal and a fatty acid layer. The fatty acid layer works a surfactant and provides a specific targeting feature for the diamond crystal. The feature of the surfactant makes the diamond crystal being easily dispersed in biological surrounding (e.g., phosphate saline buffer) and the feature of specific targeting ability provides the diamond crystal with specific recognizing specific targets. This invention allows researchers to use diamond crystal as a marker for specific labelling.

19 Claims, 24 Drawing Sheets

(56) References Cited

OTHER PUBLICATIONS

Slegerova, J., et al., "Designing the nanobiointerface of fluorescent nanodiamonds: highly selective targeting of glioma cancer cells", *Nanoscale*, 2015, pp. 415-420, vol. 7.

Sotoma, S., et al., "Suppression of Nonspecific Protein-Nanodiamond Adsorption Enabling Specific Targeting of Nanodiamonds to Biomolecules of Interest", *Chemistry Letters*, 2015, pp. 354-356, vol. 44.

Sotoma, S., et al., "Selective Labeling of Proteins on Living Cell Membranes Using Fluorescent Nanodiamond Probes", *Nanomaterials*, 2016, 9 pages, vol. 6, Issue 56.

Chang, B., et al., "Highly Fluorescent Nanodiamonds Protein-Functionalized for Cell Labeling and Targeting", *Advanced Functional Materials*, 2013, pp. 5737-5745, vol. 23.

Moore, L., et al., "Diamond-Lipid Hybrids Enhance Chemotherapeutic Tolerance and Mediate Tumor Regression", *Advanced Materials*, 2013, pp. 3532-3541, vol. 25.

Vitale, S. and Katz, J., "Liquid Droplet Dispersions Formed by Homogeneous Liquid-Liquid Nucleation: "The Ouzo Effect"", *Langmuir*, 2003, pp. 4105-4110, vol. 19.

Beck-Broichsitter, M., et al., "Solvent selection causes remarkable shifts of the "Ouzo region" for poly(lactide-co-glycolide) nanoparticles prepared by nanoprecipitation", *Nanoscale*, 2015, pp. 9215-9221, vol. 7.

Nicolas, J., "Drug-Initiated Synthesis of Polymer Prodrugs: Combining Simplicity and Efficacy in Drug Delivery", *Chemistry of Materials*, 2016, pp. 1591-1606, vol. 28.

Chiu, S., et al., "Silica Ouzo Effect: Amphiphilic Drugs Facilitate Nanoprecipitation of Polycondensed Mercaptosilanes", *Langmuir*, 2016, pp. 211-220, vol. 32.

Hsieh, F., et al., "Correlative Light-Electron Microscopy of Lipid-Encapsulated Fluorescent Nanodiamonds for Nanometric Localization of Cell Surface Antigens", *Analytical Chemistry*, 2018, pp. 1566-1571, vol. 90.

Grimaldi, N., et al., "Lipid-based nanovesicles for nanomedicine", *Chem. Soc. Rev.*, 2016, pp. 6520-6545, vol. 45.

Mochalin, V., et al., "The properties and applications of nanodiamonds", *Nature Nanotechnology*, 2012, pp. 11-23, vol. 7.

Verwey, E., "Theory of the Stability of Lyophobic Colloids", Symposium on the Stability of Colloidal Dispersions, 110th Meeting of the American Chemical Society, Sep. 1946. Chicago, Illinois, USA.

Sotoma, S., et al., "Highly stable lipid-encapsulation of fluorescent nanodiamonds for bioimaging applications", *Chem. Commun.*, 2018, pp. 1000-1003, vol. 54.

Su, L., et al., "Fluorescent nanodiamonds enable quantitative tracking of human mesenchymal stem cells in miniature pigs", *Scientitific Reports*, 2017, 11 pages.

Davis, K., et al., "Determination of CD4 Antigen Density on Cells: Role of Antibody Valency, Avidity, Clones, and Conjugation", *Cytometry*, 1998, pp. 197-205, vol. 33.

Pannu, K., et al., "Performance Evaluation of QuantiBRITE Phycoerythrin Beads", *Cytometry*, 2001, pp. 250-258, vol. 45.

Wilson, K., et al., "Single particle tracking of cell-surface HLA-DR molecules using R-phycoerythrin labeled monoclonal antibodies and fluorescence digital Imaging", *Journal of Cell Science*, 1996, pp. 2101-2109, vol. 109.

Morrison, I., et al., "Detecting and Quantifying Colocalization of Cell Surface Molecules by Single Particle Fluorescence Imaging", *Biophysical Journal*, 2003, pp. 4110-4121, vol. 85.

Johnson, E., et al., "Correlative in-resin super-resolution and electron microscopy using standard fluorescent proteins", *Scientific Reports*, 2015, 9 pages.

Perkovic, M., et al., "Correlative Light- and Electron Microscopy with chemical tags", *Journal of Structural Biology*, 2014, pp. 205-213, vol. 186.

Zhang et al., "Photoacoustic emission from fluorescent nanodiamonds enhanced with gold nanoparticles," Biomedical Optics Express, Jul. 1, 2012, Vo. 3, No. 7, pp. 1662-1669.

Chen, Pei-Hsin, "Developing and application of the growth hormone-nanodiamond complex," Institute of Biochemical Engneering of National Chiao Tung University, Jul. 2007, 66 pages.

Lombardo et al., "Soft Interaction in Liposome Nanocarriers for Therapeutic Drug Delivery," Nanomaterials, 2016, vol. 6, No. 125, 26 pages.

Office Action issued in corresponding TW application No. 107118058 dated Mar. 19, 2021 (6 pages), English portions only.

Tan, Huanshu et al., "Evaporation-triggered microdroplet nucleation and the four life phases of an evaporating Ouzo drop," PNAS Aug. 2, 2016, 113(31), 8642-8647 (6 pages).

* cited by examiner

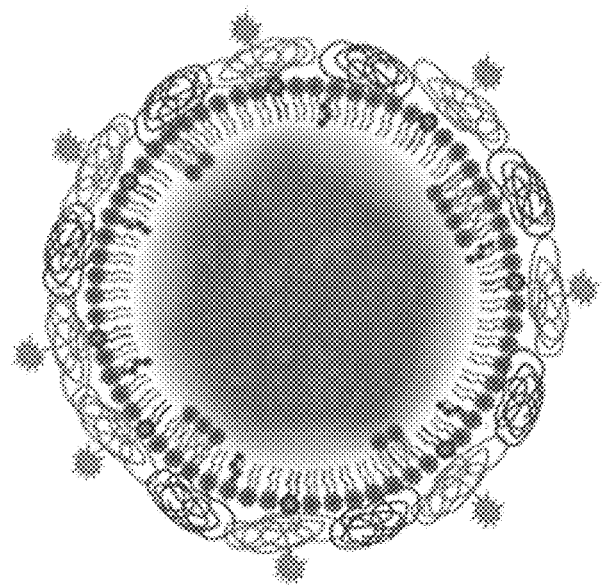
FIG. 1B
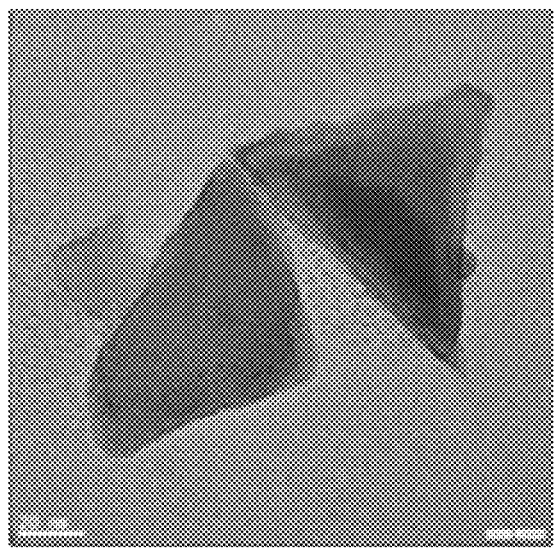 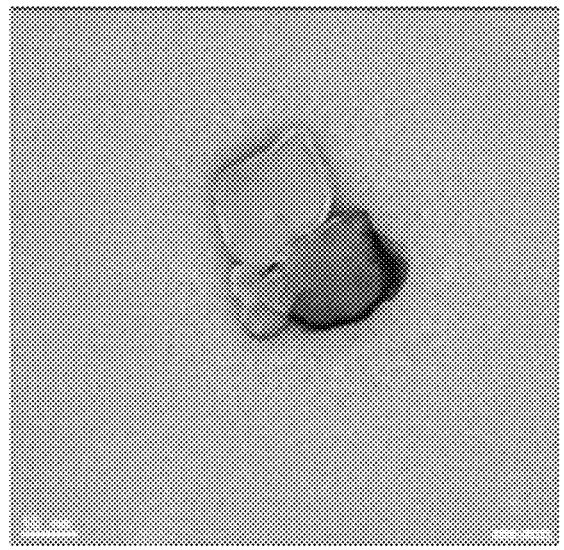
FIG. 2A　　　　　　　　　FIG. 2B

Diyne PC:

Cholesterol:

ENCAPSULATED FUNCTIONALIZED DIAMOND CRYSTAL

CROSS REFERENCE OF RELATED APPLICATIONS

This non-provisional application claims priority to U.S. provisional patent application Ser. No. 62/511,034 filed on May 25, 2017. This and all other extrinsic materials discussed herein are hereby incorporated by reference in their entirety.

BACKGROUND

Technical Field

This invention herein is a functionalized diamond crystal with high dispersibility in physiological and/or with specific targeting ability, which is an improvement of diamond crystal.

Related Arts

Firstly, it should be noted that all publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The surface of a cell is covered with various types of antigens. These antigens serve as molecular markers for the identification of different cell types as well as the targets for diagnosis and therapy. Red blood cells, for instance, are classified according to the inherited differences in cell surface antigens made of polysaccharides.[1] The human leukocyte antigens (or CD antigens), on the other hand, are made of membrane proteins that play a significant role in immune response.[2] The significance of these molecules has stimulated the development of cell-enzyme-linked immunosorbent assay (cell-ELISA) as an immunoenzymatic technique for quantitative analysis of antigens expressed on cell surface.[3] However, the method could not provide any information on the localization of the antigens of interest on cell surface. Conversely, atomic force microscopy[4] and optical microscopy serve well the latter purpose,[5,6] but they could not determine the antigen concentration with sufficient accuracy.

Fluorescent nanodiamonds (FNDs) are carbon-based nanoparticles containing a high-density ensemble of negatively charged nitrogen-vacancy (NV$^-$) defects as fluorescent centers.[7] Distinct from molecular fluorophores such as organic dyes and fluorescent proteins, the NV$^-$ centers are photostable, magneto-optical, and have a relatively long fluorescence lifetime of ~20 ns in water and physiological medium.[8] They are embedded deep in the chemically inert diamond matrix and thus protected from the environment. Their fluorescence properties are largely unaffected by strong acid and strong base treatments in aqueous solution at room temperature.[9] The preservation of these unique characteristics has enabled background-free imaging and detection of FNDs in cell and tissue samples by time gating and magnetic modulation.[10-12] It provides a robust new tool for absolute quantification and nanoscale localization of the surface antigens of live cells.

In applying FNDs as photostable agents for antigen targeting, there are two hurdles to overcome: (1) particle agglomeration in cell medium and (2) nonspecific binding of the agents with undesired protein molecules on cell surface, both of which will lead to false positive results. A number of attempts have been made to address these two issues.[13-16] Methods developed include covalent conjugation of polymers such as hyperbranched polyethylene glycol (PEG)[15,16] or poly[N-(2-hydroxypropyl)methacrylamide][13,14] with carboxylated FNDs to form highly biocompatible protein-resistant coating. Although Chang et al.[17] have applied the former approach and its variance to synthesize PEGylated biotinylated FNDs to label CD44 antigens on human hepatoma cell lines, a more general and effective method is desired.

SUMMARY

To overcome those limitations mentioned as above, this disclosure has developed a technology that allows not only absolute quantification of the cell surface antigens but also spatial localization of these antigens with nanometric resolution. In comparison with cell-ELISA, the method involves no enzymes, radioactive materials, and antigen extraction. The key component of this new technology is the lipid encapsulated fluorescent nanodiamond (FND).

This invention herein is a functionalized diamond crystal with high dispersibility in physiological solution and/or with specific targeting ability, which is an improvement of diamond crystal. To equip diamond crystal with a targeting feature, the surface of the diamond crystal is modified by adding desired functional groups (e.g., biotin, antibody and etc.). After modification, the functionalized diamond crystal is able to recognize specific biomass and maintain good dispersion in bio-fluid surrounding.

This invention can be applied to specific targeting, bio-labelling, bio-imaging both in vitro and in vivo. Compared to the commercial bio-imaging reagent, the diamond crystal based bio-imaging reagent can also be utilized in light microscopy, electron microscopy, or correlative light-electron microscopy (CLEM) owing to its stable luminescence centers.

Moreover, this disclosure presents a simple and effective method to encapsulate FNDs in bio-functionalized lipid layers. Instead of using the thin-film hydration technique[18], this disclosure takes advantage of the Ouzo effect,[19] which is a spontaneous emulsification phenomenon that has been utilized as a tool in many fields of research such as synthesis of polymeric nanocapsules and prodrugs.[20-22] It involves the addition of a mixture of hydrophobic solute and water-miscible solvent into water to form stable microdroplets. These droplets can serve as carriers for compounds of interest, such as FNDs. The hydrophobic solute used in this work is a lipid layer composed of egg phosphatidylcholine, PEGylated 1,2-distearoyl-sn-glycero-3-phosphoethanolamine, and cholesterol (FIG. 1)[23]. They are dissolved in tetrahydrofuran (i.e. the water-miscible solvent) and then added to water containing surface-oxidized FNDs to form emulsions. Subsequent evaporation of tetrahydrofuran in vacuum allows the lipid layer to coat on FND. The method enables not only robust coating but also synthesis of lipid-coated FNDs with desired functional groups such as biotin. The particles exhibit high dispersibility in phosphate-buffered saline (PBS) and cell medium, well suited for specific antigen labeling and targeting applications.

To achieve the above objective, one embodiment of the invention discloses a nanodiamond particle complex comprising an amphiphilic capsule and a nanodiamond particle encapsulated in said amphiphilic capsule. The amphiphilic capsule comprises a plurality of fatty acid molecules forming a single-layered, a partial-single layered, or micelle-like structure, and the nanodiamond particle has at least one nitrogen-vacancy center.

To achieve the above objective, one embodiment of the invention discloses a reagent kit for targeting a biological sample. The reagent kit comprises the nanodiamond particle complexes as described above, which is configured to be able to specifically recognize the biological sample.

To achieve the above objective, one embodiment of the invention discloses a method for targeting a biological sample. The method comprises the step of treating the biological sample with the nanodiamond particle complexes as described above which is configured to be able to specifically recognize said biological sample.

To achieve the above objective, one embodiment of the invention discloses a use of the nanodiamond particle complex as described above as a labeling agent in light microscopy, electron microscopy or correlative light-electron microscopy.

To achieve the above objective, one embodiment of the invention discloses a use of the nanodiamond particle complex as described above to quantify a specific molecule in a sample.

To achieve the above objective, one embodiment of the invention discloses a method to quantify a concentration of the nanodiamond particle complex as described above in a sample, comprising: providing the sample to be tested; applying the nanodiamond particle complex to the sample; and measuring a fluorescent signal emitted by the nanodiamond particle complex so as to determine the concentration of the nanodiamond particle complex in the sample.

To achieve the above objective, one embodiment of the invention discloses a method for imaging a sample. The method comprises the following steps: labelling a sample with a nanodiamond particle complex as described above; irradiating the labelled sample with an exciting energy; and generating an image of at least a portion of the sample based on a signal collected from the excited sample, wherein the luminescent diamond particle, 1 nm to 1 mm in diameter, has at least one nitrogen-vacancy center.

Accordingly, the present disclosure provides a nanodiamond particle complex, a reagent kit comprising such nanodiamond particle complex for targeting a biological sample, and a method for targeting a biological sample by using such nanodiamond particle complexes. As evidenced by the following data, the nanodiamond particle complexes provided by this disclosure have been demonstrated to be a biocompatible nanoprobe with unique magneto-optical properties, including exceptionally high photostability, magnetically modulable fluorescence intensity, and longlived fluorescence lifetime. These properties together make it possible to achieve high-quality and background-free imaging and localization of cellular components with nanoscale resolution if the nanoparticles are endowed with specific targeting abilities. This work demonstrates that FNDs surface-oxidized in air can be facilely encapsulated in lipids by utilizing the Ouzo effect, and these lipid-encapsulated FNDs are useful as specific cell targeting agents after proper conjugation of the lipid layers with bioactive molecules such as biotin. These lipid-encapsulated FNDs have been applied for absolute quantification and nanoscale localization of CD44 antigens on HeLa cell membrane with CLEM to prove the principle. The method is general and applicable to other biomolecules since a variety of lipid derivatives are now commercially available and they all serve well the purpose after minor modification of the protocols illustrated in this work.

BRIEF DESCRIPTION OF THE DRAWINGS

The embodiments will become more fully understood from the detailed description and accompanying drawings, which are given for illustration only, and thus are not limitative of the present invention, and wherein:

FIGS. 1A-1B. Structure of a biotinylated lipid-coated FND (bL-FND).

FIGS. 2A-2E. (FIGS. 2A, 2B) TEM images of 100 nm FNDs without (FIG. 2A) or with (FIG. 2B) lipid coating. (FIGS. 2C, 2D and 2E) Size distributions of 100 nm (FIG. 2C), 50 nm (FIG. 2D) and 35 nm (FIG. 2E) FNDs before and after coating with lipids in DDW or PBS.

(FIG. 6A) Fluorescence spectra of 35-nm FNDs in water before and after magnetic modulation. The FND concentration is 5 μg/mL. (FIG. 6B) Quantification of CD44 antigen on HeLa cell surface. The amount of CD44 determined decreases with the increase of the bL-FND particle size from 35, 50, to 100 nm in diameter. The particle concentrations used in the labeling are all 100 μg/mL, and the relative numbers of the particles are given in the right vertical axis. Blue arrow denotes the result obtained with the PE assay. (FIG. 6C) Flow cytometry analysis of HeLa cells labelled with biotin-anti-CD44 antibody, neutravidin and 35 nm of bL-FND. Control experiments were performed following the same labelling procedure but without neutravidin (blue) or biotin-anti-CD44 antibody (orange) and cell only represents in grey.

Zoom-in SEM image and (i) CLEM image obtained by superimposing images in (f) and (h). The tilt angle to achieve complete overlap of the FNDs is 23°. (j-l) Nonlinear transformation of the LM image (c) with the eC-CLEM software. The deformed grid used to perform the nonlinear transformation is given in (j) and the resulting LM and CLEM images are shown in (k) and (l), respectively. Scale bars: 20 μm (a, b, d, e, g) and 5 μm (c, f, h, i).

Figure 10:
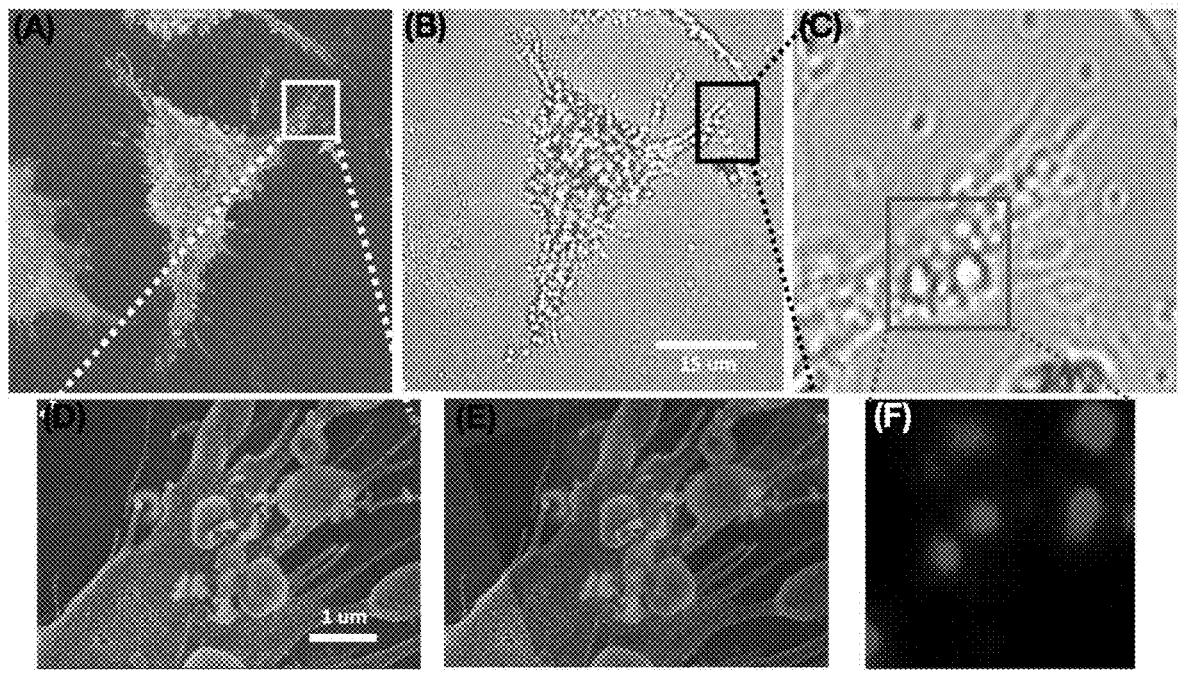

FIG. 10. (a and d) SEM, (b) bright field, (c) zoom-in of (b), (f) fluorescence, and (e) CLEM images of vaccinia virus infected HeLa cells labelled with biotin anti-vaccinia virus antibody, neutravidin, and then bL-FNDs.

Figure 11:
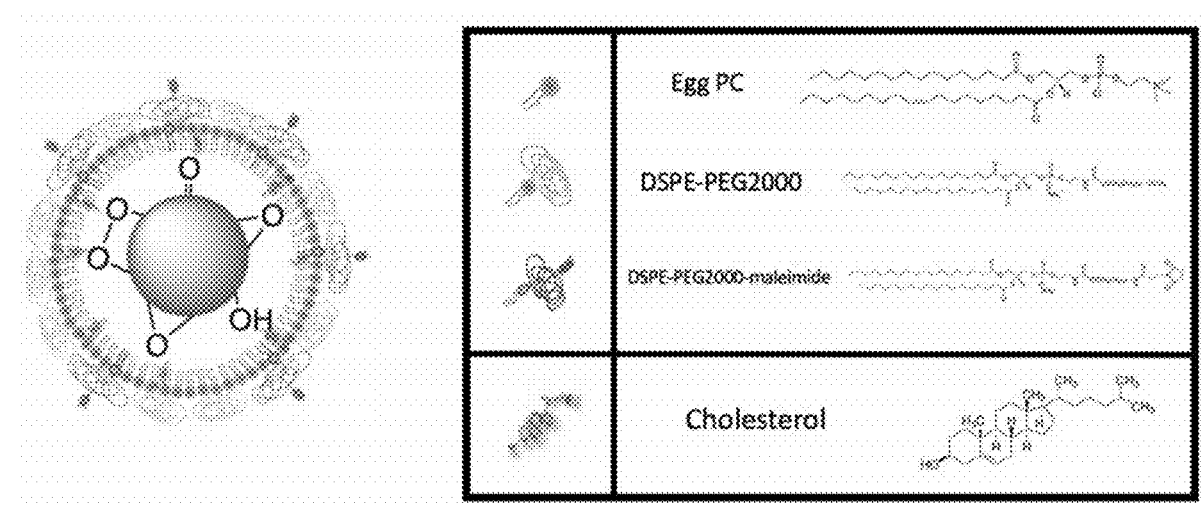

FIG. 11. Structure of a lipid-coated FND according to another embodiment of the present invention.

Figure 12:
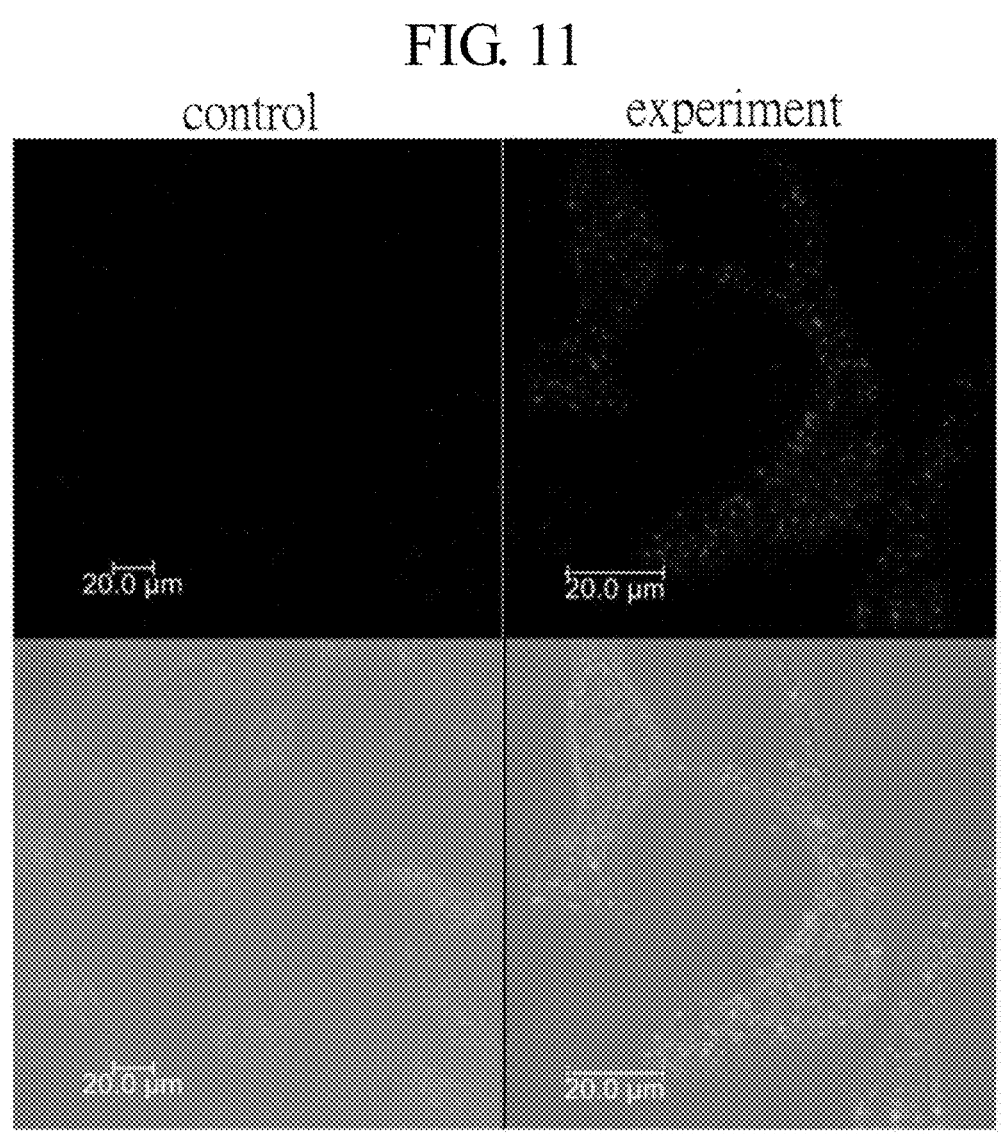

FIG. 12. Immunostaining images of HeLa cells labelled with anti-CD44 antibodies conjugated maleimide-modified lipid-coated FNDs (left panel: control result; right panel: experimental result).

Figure 13:
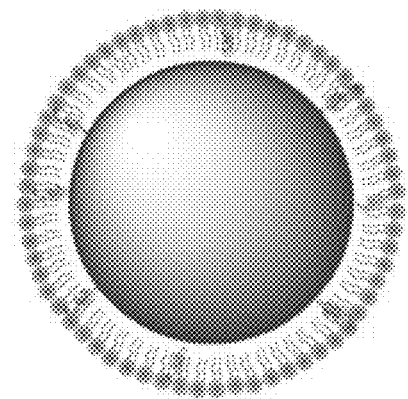
Figure 13:
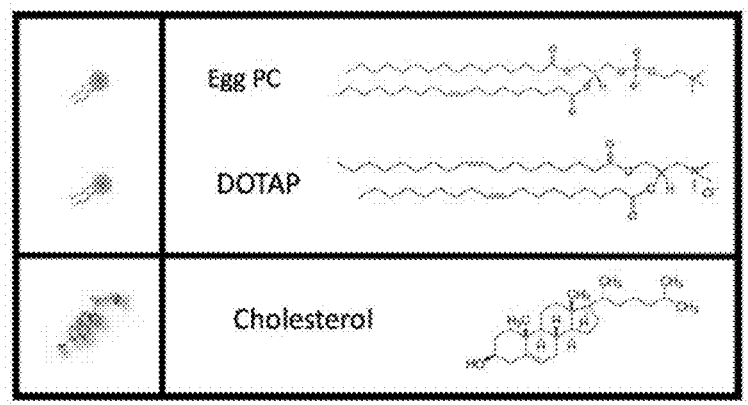

FIG. 13. Structure of a lipid-coated FND according to yet another embodiment of the present invention.

Figure 14:
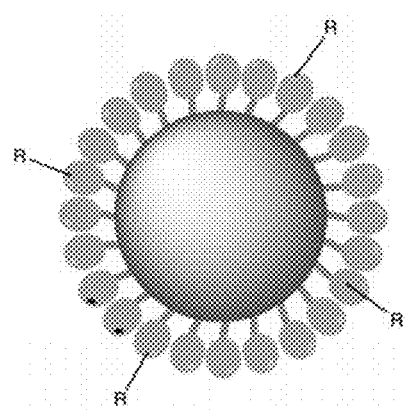
Figure 14:
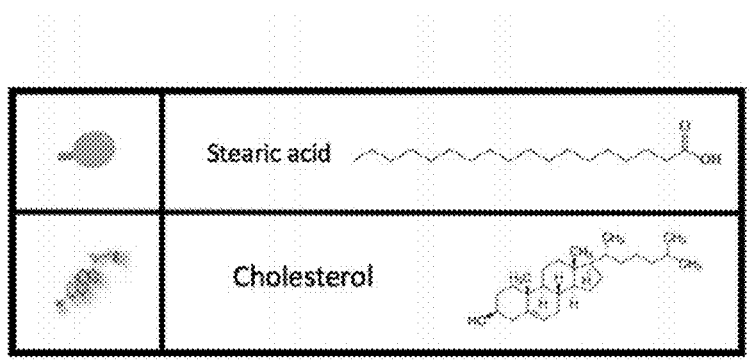

FIG. 14. Structure of a lipid-coated FND according to still another embodiment of the present invention.

Figure 15:
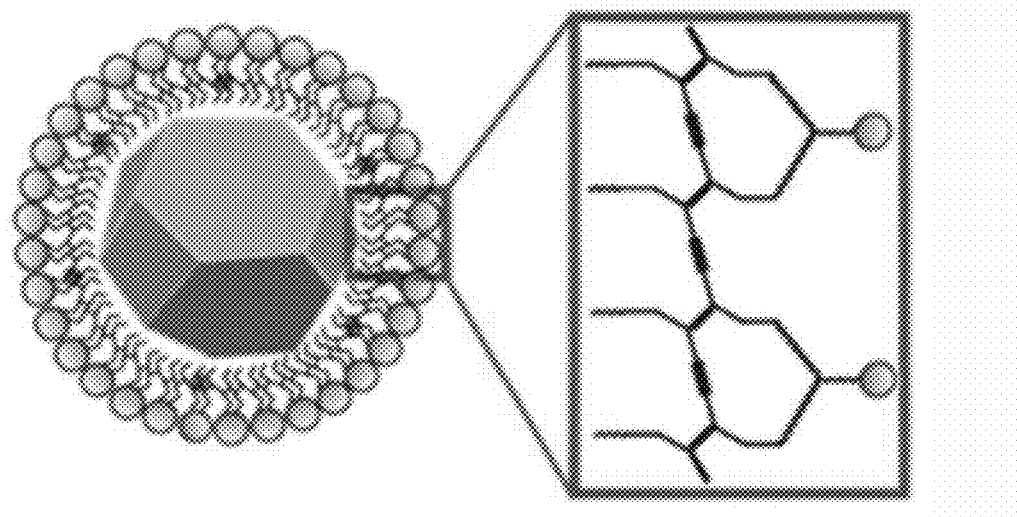
Figure 15:
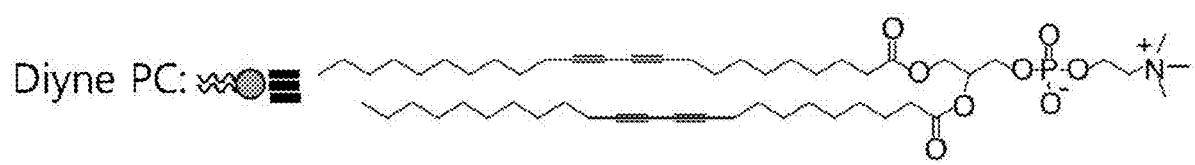
Figure 15:
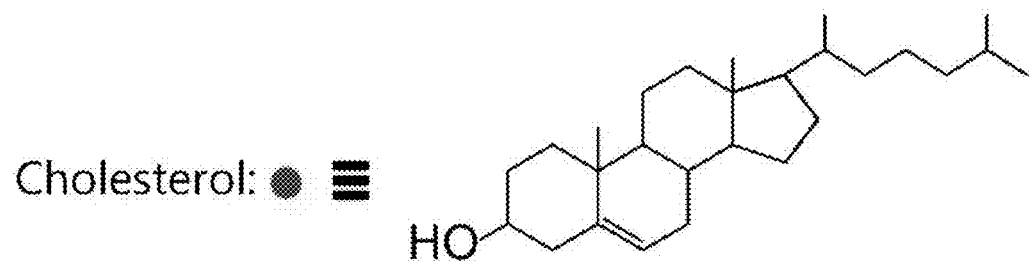

FIG. 15. Structure of a lipid-coated FND according to still another embodiment of the present invention.

Figure 16:
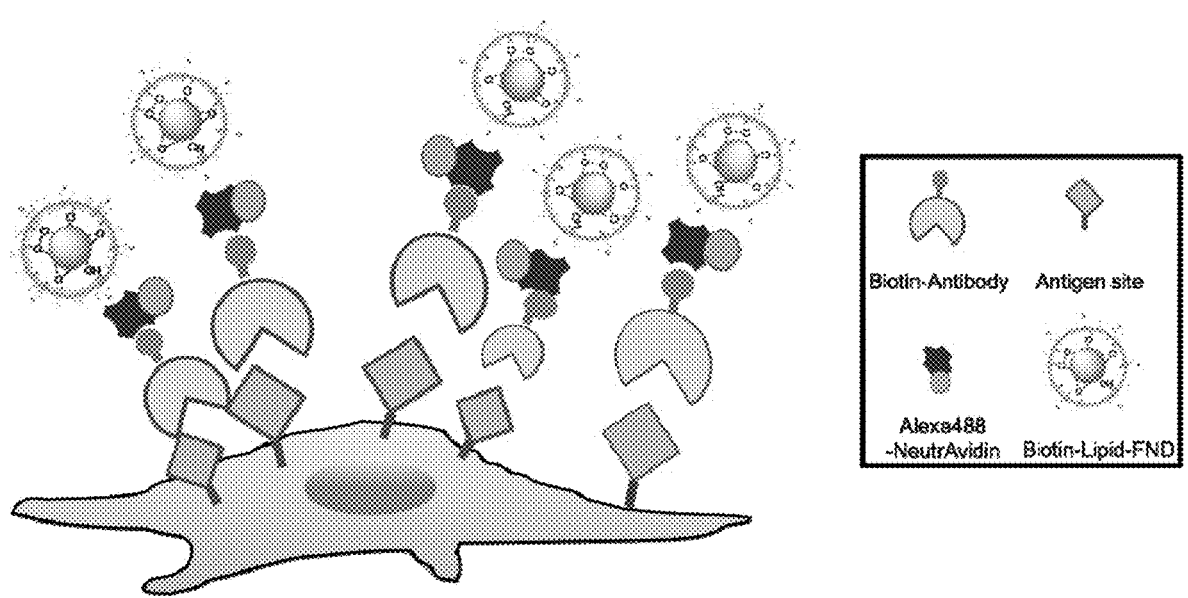

FIG. 16. The strategy of B-FND labelling experiment in vitro.

Figure 17:
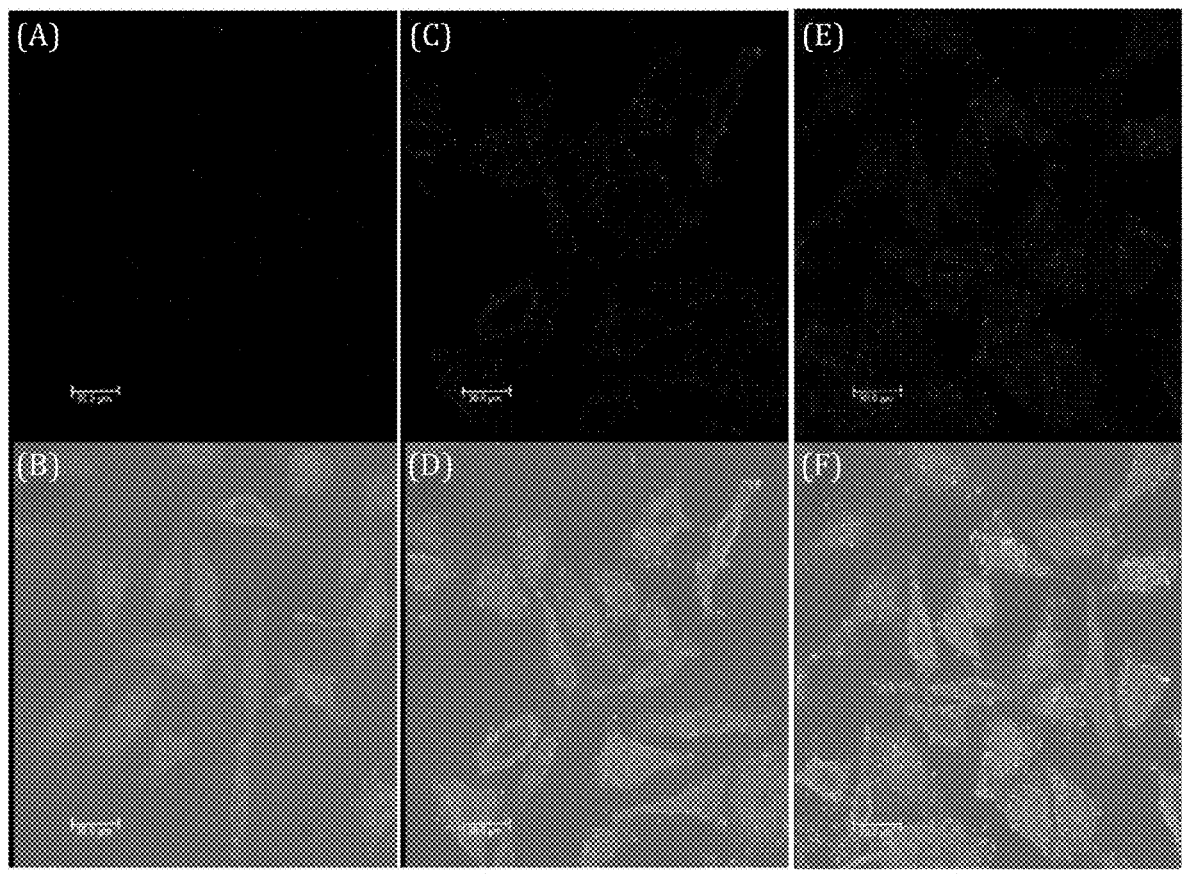

FIG. 17. Bright-field and confocal microscopy images of HeLa cells labelled with 100 nm of bL-FNDs consisting of various molar percentages of biotin. The images of cells labelled with bL-FND containing (A&B) 0%, (C&D) 0.5%, and (E&F) 1% of biotin. The upper panels show the signal from FND and the bottom panels represent the co-localization of bL-FNDs, DyLight®488-NA and CD44 antigens.

Figure 18:
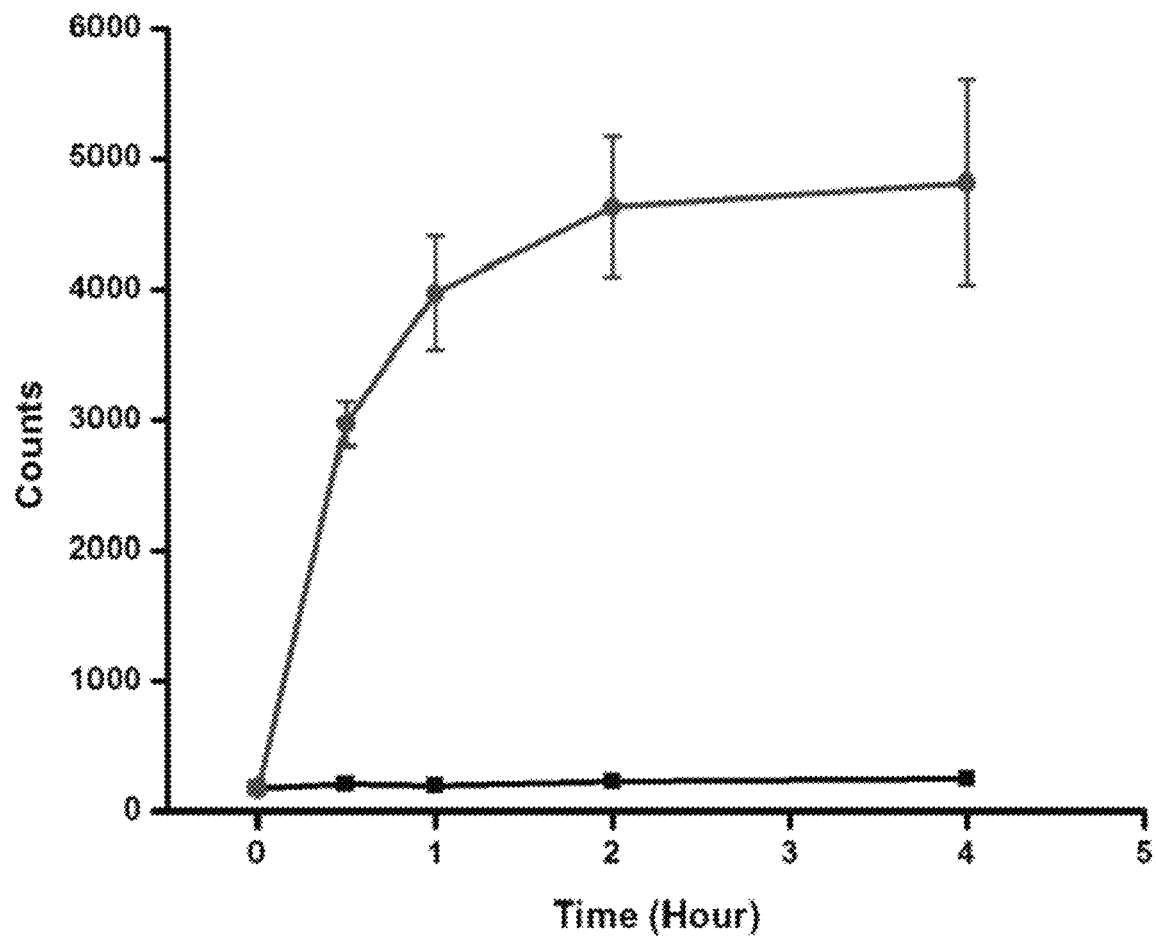

FIG. 18. Mean red fluorescence intensity from cells labelled with 100 μg/mL of 100 nm bL-FND containing 1% of biotin for 0, 0.5, 1, 2 and 4 h. The red curves serve as cells labelled with biotin-anti-CD44 antibody, neutravidin and bL-FND and the black curves represent cells labelled with biotin-anti-CD44 antibody and bL-FND. Error bars represent three independent experiments.

Figure 19:
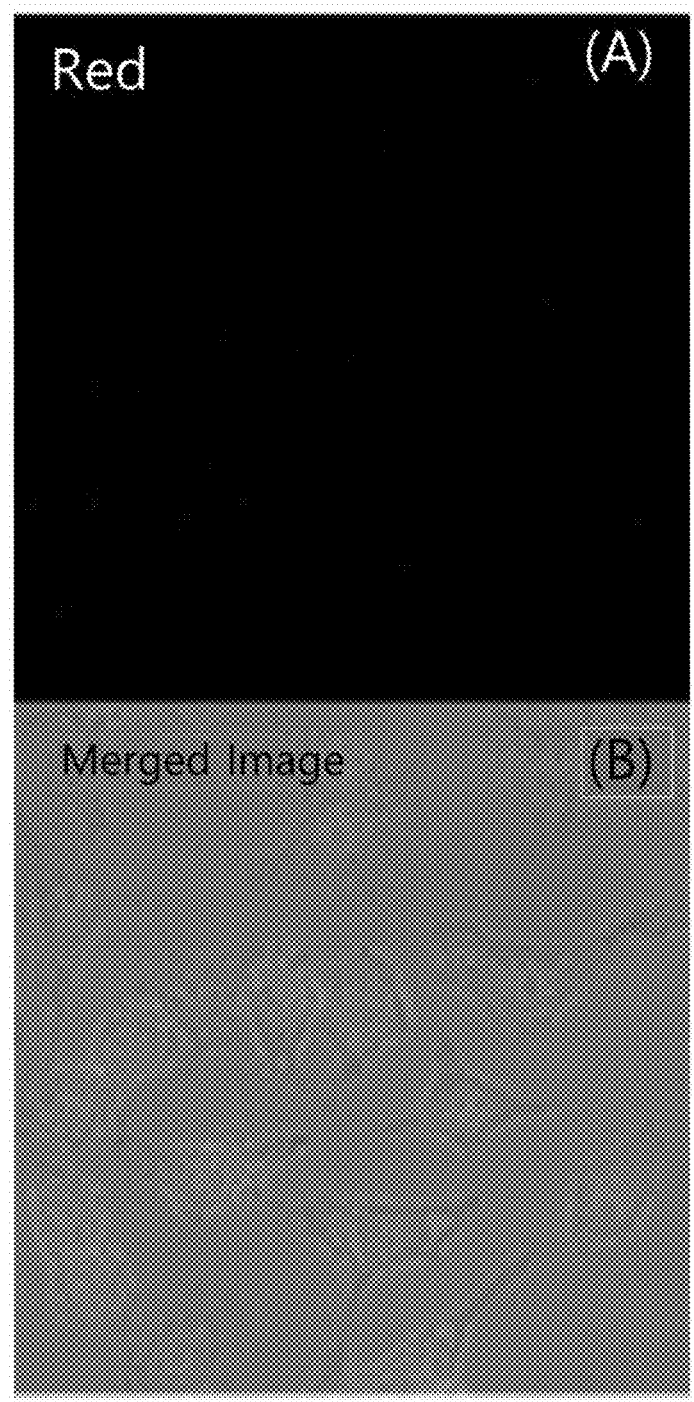

FIG. 19. (A) Confocal microscopy and (B) bright-field images of HeLa cells labelled with 100 nm of bL-FNDs containing 1% of DSPE PEG200 biotin without DyLight®488-NA.

Figure 20:
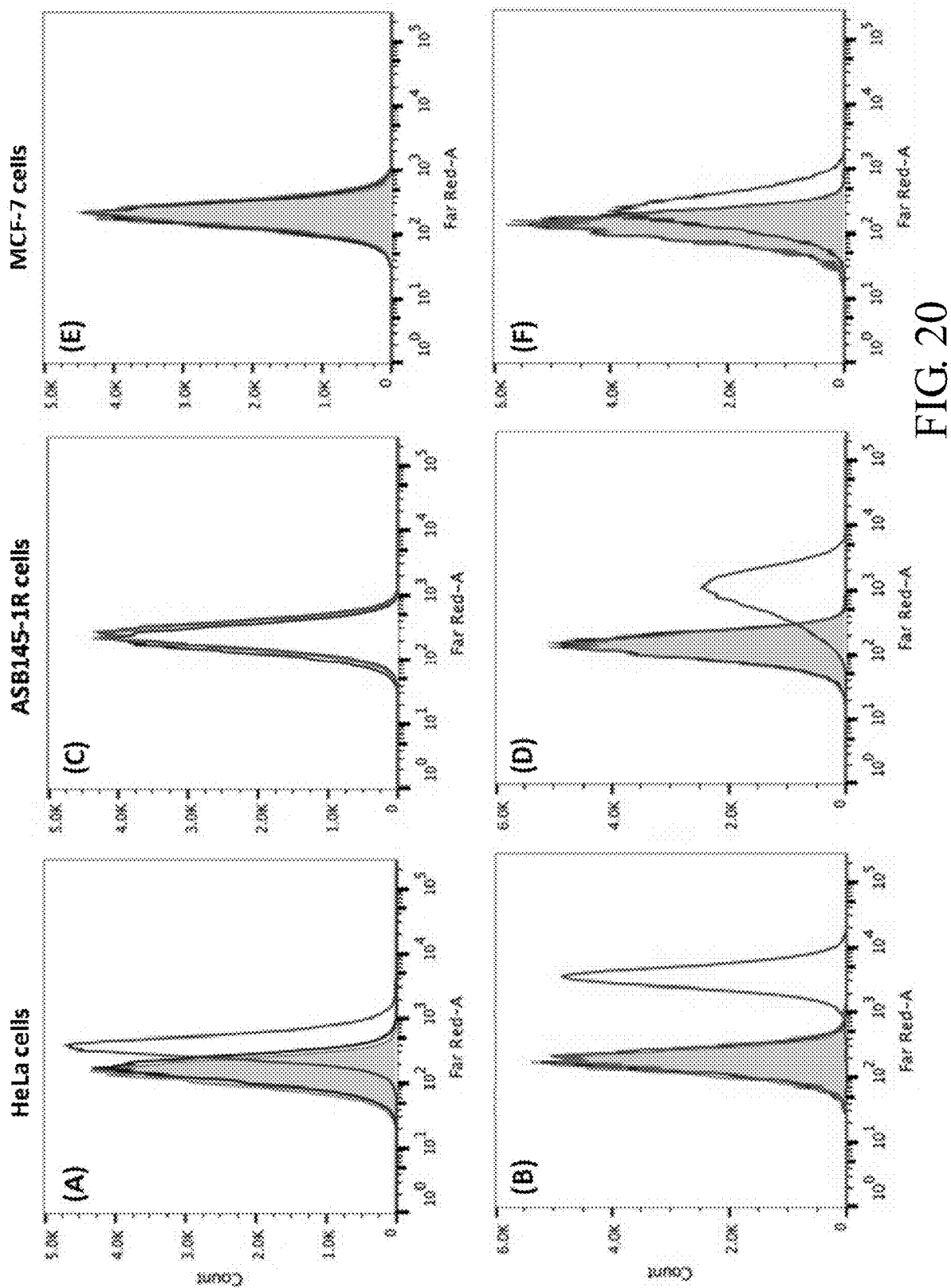

FIG. 20. Flow cytometric analysis of HeLa (A&B), ASB145-1R (C&D), and MCF7 (E&F) cells labelled with biotin-anti-CD44 antibody, neutravidin, and bL-FND (B, D, F) or biotinAtto542 (A, C, E), respectively. Control experiments were performed following the same labelling procedures but without neutravidin (blue) or biotin-anti-CD44 antibody (orange). Cell-only results are given in grey.

Figure 21:
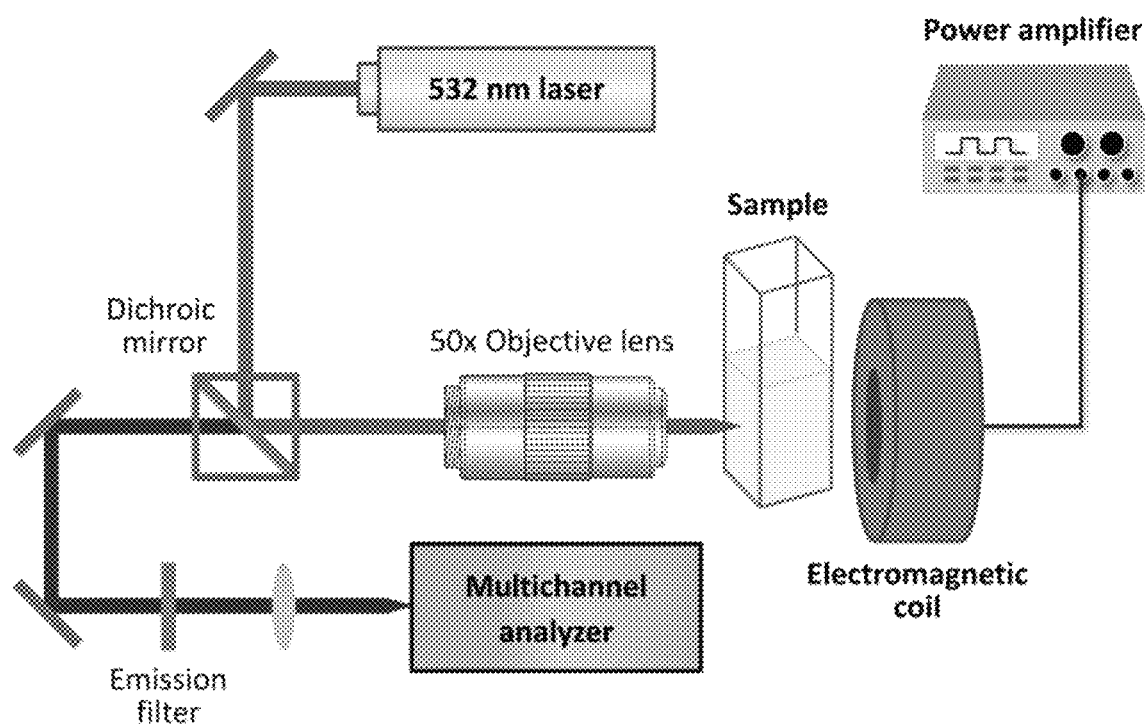

FIG. 21. Experimental setup of the magnetic lock-in detection fluorescence spectrometer for ultrasensitive quantification of FNDs in cells and tissues.

DETAILED DESCRIPTION OF THE INVENTION

The embodiments of the invention will be apparent from the following detailed description, which proceeds with reference to the accompanying drawings, wherein the same references relate to the same elements.

Certain exemplary embodiments according to the present disclosure are described as below.

Nanodiamond Particle Complex

One embodiment of the disclosure provides a nanodiamond particle complex comprising an amphiphilic capsule and a nanodiamond particle encapsulated in said amphiphilic capsule. The amphiphilic capsule comprises a plurality of fatty acid molecules forming a single-layered, a partial-single layered, or micelle-like structure. The size of the composition of nanodiamond particle complex may distribute from 1 nm to 1 μm in diameter. The nanodiamond particle may have at least one nitrogen-vacancy center, and each fatty acid molecule may form covalent link with nearby fatty acid molecule(s).

In this embodiment, at least one of the fatty acid molecules in the nanodiamond particle complex can be modified with a functional group which is configured to graft a recognizing molecule, and such recognizing molecule is configured to be able to specifically recognize a biological sample. However, in this embodiment, it also possible that none of the fatty acid molecules is modified with any functional groups mentioned above. Moreover, it is found that such nanodiamond particle complex may have a high dispersity in a physiological solution or a high ionic strength solution, even all the fatty acid molecules is not modified with the functional groups. The functional group can be a hydroxyl group, a carboxyl group, a biotin moiety, a cyanuric chloride modified group, a thiol group, a maleimide group, an alkyne group, an azide group, an antibody, a halo ligand, or any combination thereof. Moreover, the fatty acid molecules can be a saturated fatty acid, an unsaturated fatty acid, a phospholipid, a glycol, a cholesterol, or any combination thereof. The aforementioned phospholipid can be, for example but not limited thereto, a phosphatidylethanolamine, Phosphatidylglycerol, Lyso Lipids, Phosphatidic acid, Sphingolipids, Phosphatidylserine, 1,2-bis(10,12-tricosadiynoyl)-sn-glycero-3-phosphocholine, 1-palmitoyl-2-(10,12-tricosadiynoyl)-sn-glycero-3-phosphoethanolamine, 1-palmitoyl-2-(10,12-tricosadiynoyl)-sn-glycero-3-phosphocholine, 1-palmitoyl-2-(10,12-tricosadiynoyl)-sn-glycero-3-phosphoethanolamine, or any combination thereof.

In this embodiment, the amphiphilic capsule may further comprise PEGylated 1,2-distearoyl-sn-glycero-3-phosphoethanolamines (DSPEs) or 10,12-Tricosadiynoic acid. And, at least a portion of (or all of) the PEGylated 1,2-distearoyl-sn-glycero-3-phosphoethanolamines or the 10,12-Tricosadiynoic acid can be labeled with functional groups, and the functional groups can be a hydroxyl group, carboxyl group, a biotin moiety, a cyanuric chloride modified group, a thiol group, a maleimide group, an alkyne, an azide group, an antibody, a halo ligand, or any combination thereof. When the functional group is a biotin moiety (i.e., "biotin-labeled" or "biotin-conjugated" or "biotinylated"), the molar ratio of biotin moiety is preferably greater than 0% and no more than 20%. In addition, the PEGylated 1,2-distearoyl-sn-glycero-3-phosphoethanolamines are PEG2000-DSPEs and the content ratio between the biotin-labeled PEG2000-DSPEs (biotin-PEG2000-DSPEs) and PEG2000-DSPEs not labeled with biotins (PEG2000-DSPEs) may range from 1:0.001 to 1:1000.

Reagent Kit

Another embodiment of this disclosure provides a reagent kit for targeting a biological sample. The reagent kit comprises the nanodiamond particle complex as described in the foregoing embodiment, and the nanodiamond particle complex is configured to be able to specifically recognize the biological sample. The biological sample can be a cell, a virus, a fragment of nucleic acids, a peptide, a hapten, an antigen, a tissue, or any combination thereof. The concentration of the composition of nanodiamond particle complex preferably ranges from 0.01 to 2000 μg/mL. More specifically, the concentration of the nanodiamond particle complex may be 100 µg/mL and the nanodiamond particle complex may comprise 1% of biotin-PEG2000-DSPE and 9% of PEG2000-DSPE.

In this embodiment, the reagent kit may further comprise a recognizing molecule (such as an antibody) which is configured to be able to specifically recognize the biological sample, and a grafting molecule which is configured to be able to bind with said recognizing molecule and said nanodiamond particle complex. The grafting molecule may be an avidin-class compound, such as avidin, streptavidin, or neutravidin. Moreover, the avidin-class compound may be further conjugated with a fluorescent compound, such as DyLight®488.

Moreover, the various configurations of the nanodiamond particle complex are substantially similar with those described in the foregoing embodiments. Therefore, the detailed explanation is omitted here.

Method for Targeting a Biological Sample

Also, this disclosure further provides another embodiment which is a method for targeting a biological sample. The method comprises the step of treating the biological sample with the nanodiamond particle complex as described in the foregoing embodiment. Such nanodiamond particle complex is configured to be able to specifically recognize said biological sample. The biological sample may be a cell, a virus, a fragment of nucleic acids, a peptide, a hapten, an antigen, a tissue, or any combination thereof.

In this embodiment, the method may further comprise the step of: sequentially treating the biological sample with a first reagent comprising an recognizing molecule (e.g., an antibody) which is configured to be able to specifically recognize said biological sample, a second reagent comprising a grafting molecule (e.g., an avidin-class compound) which is configured to be able to bind with said antibody, and then performing the step of treating the biological sample with the nanodiamond particle complexes as described above.

Next, the method may further comprise a step of washing unbound and non-specifically binding recognizing molecule with a suitable wash buffer.

Next, the method may further comprise a step of washing unbound grafting molecules with a suitable wash buffer.

Next, the method may further comprise a step of washing unbound and non-specifically binding nanodiamond particle complexes with a suitable wash buffer.

Next, the method may further comprise a step of exposing said biological sample to an energy source after being treated with said first reagent, second reagent and third reagent. An optical signal is generated from the exposed biological sample when the antigens are recognized by the nanodiamond particle complexes through the recognizing molecule and the grafting molecule. In addition, the energy source is preferably a light which comprises a wavelength ranging from 200 nm to 1200 nm, or the energy source can be an electron beam.

Also, the method may further comprise a step of observing the biological sample treated with the nanodiamond particle complex with light microscopy, electron microscopy or correlative light-electron microscopy.

Moreover, the various configurations of the nanodiamond particle complex are substantially similar with those described in the foregoing embodiments. Therefore, the detailed explanation is omitted here.

Also, this disclosure further provides an embodiment regarding to the use of the aforementioned nanodiamond particle complex as a labeling agent in the light microscopy, electron microscopy or correlative light-electron microscopy, and an embodiment regarding to the use of the aforementioned nanodiamond particle complex to quantify a specific molecule in a sample. In addition, in the use of the aforementioned nanodiamond particle complex to quantify of the specific molecule, the quantity (or its amount) of the specific molecule can be calculated via the concentration of the nanodiamond particle complex in the sample measured with a magnetic field.

Method to Quantify a Concentration of the Nanodiamond Particle Complex in a Sample Also, this disclosure further provides another embodiment which is a method to quantify a concentration of the nanodiamond particle complex as described above in a sample. The sample may be an aqueous sample and/or a biological sample. The method comprises the following steps: providing the sample to be tested; applying the nanodiamond particle complex to the sample; and measuring a fluorescent signal emitted by the nanodiamond particle complex so as to determine the concentration of the nanodiamond particle complex in the sample.

In this embodiment, the fluorescent signal of the nanodiamond particle complex can be measured with a magnetic field.

Method for Imaging a Sample

Also, this disclosure further provides another embodiment which is a method for imaging a sample. Such comprises the following steps: labelling a sample with a nanodiamond particle complex as described above; irradiating the labelled sample with an exciting energy; and generating an image of at least a portion of the sample based on a signal collected from the excited sample, and the luminescent diamond particle, which is 1 nm to 1 mm in diameter, has at least one nitrogen-vacancy center. The signal may include fluorescence light emitted from the diamond particle in response to the exciting energy.

In this embodiment, the exciting energy may be electron, light, microwave, radio waves, infrared, X rays, gamma rays, cosmic rays, or a combination thereof.

Moreover, the various configurations of the nanodiamond particle complex are substantially similar with those described in the foregoing embodiments. Therefore, the detailed explanation is omitted here.

To illustrate the synthesis of the nanodiamond particle complexes, reagent kit comprising the same, and the methods for targeting biological samples according to the foregoing embodiments, there are several examples shown below.

Experimental Example 1: bL-FND Synthesis

The experiment began with the synthesis of lipid-coated FNDs functionalized with biotin groups (bL-FND) based on the thin-film hydration method.[24] It is found that the bL-FND prepared in this manner could be dispersed well in high ionic strength solution (such as PBS), but much non-specific targeting was present during the cell labeling (data no shown), which could be a result of incomplete lipid encapsulation of the particles. FND is a carbon-based material and its surface hydrophobicity can be properly tuned by chemical modification.[25] Phospholipid is a bipolar material, which has a hydrophilic head and two hydrophobic tails. Mixing these two compounds together should allow the hydrophobic tail of phospholipid to bind with FND and the hydrophilic head of it points toward water. Hence, in this embodiment, it has been tried to produce bL-FND by using the solvent evaporation method based on the Ouzo effect, where the lipid mixture was first dissolved in tetrahydrofuran (THF), followed by dropping the lipid solution into a FND suspension and then removing the organic solvent by vacuum evaporation.

Figure 1A:
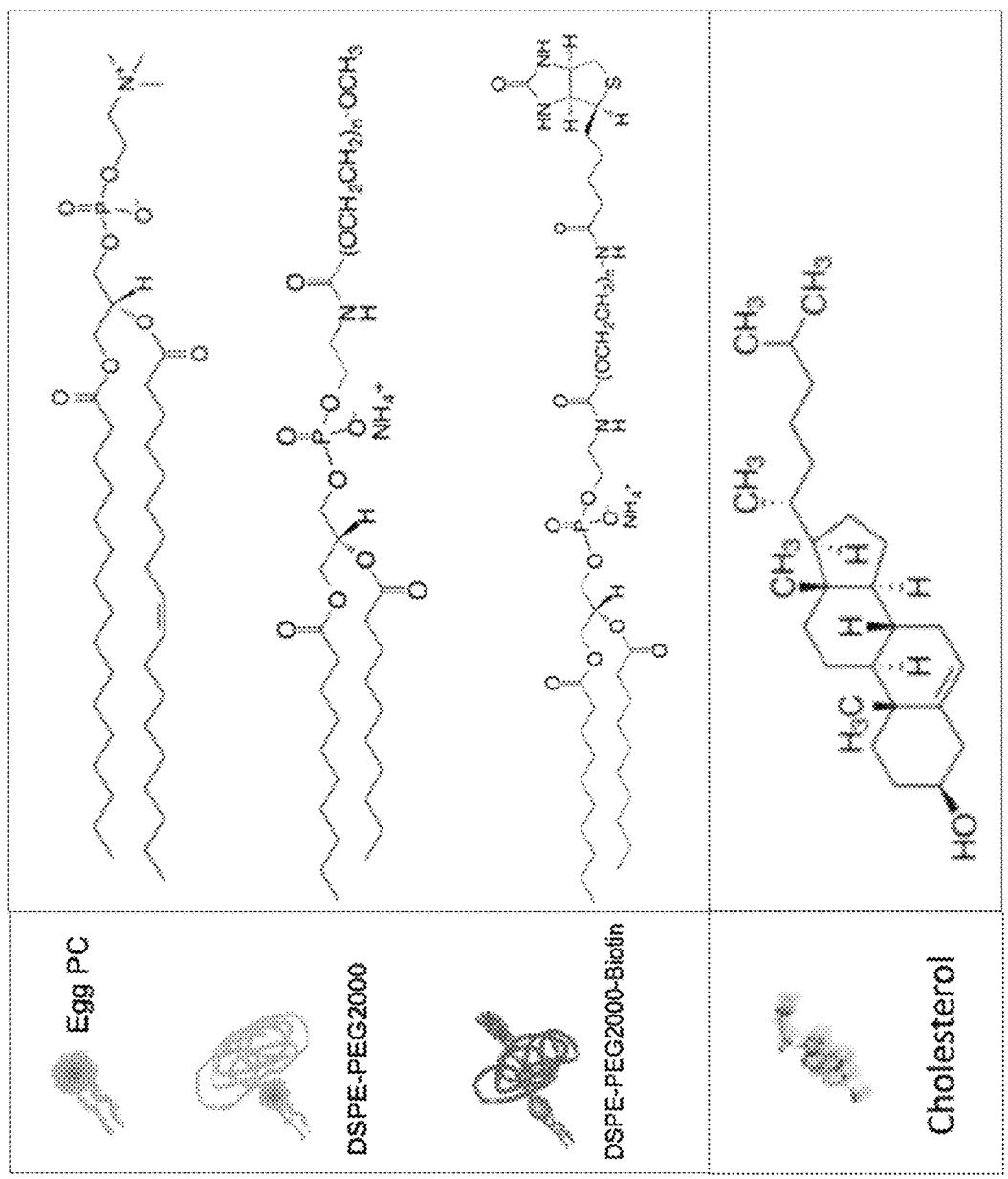
Figure 1A:
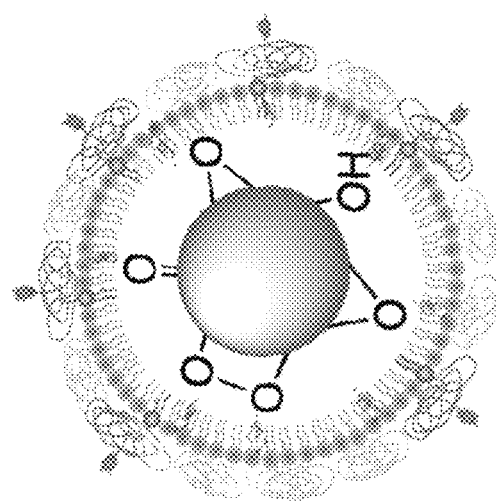

The lipid mixture used in the synthesis consisted of cholesterol (a widely used stabilizer for liposome) and phospholipid (L-α-phosphatidylcholine from chicken eggs, Egg PC) with a molar ratio of 1:1. The FNDs, on the other hand, are air-oxidized. The air oxidized of FNDs at 450° C. for 2 h effectively terminated the diamond surface with oxygen (30% of surface carbon atoms) to maintain good dispersibility of the particles in water. The rest of the $sp^3$ carbon atoms of diamonds allow the hydrophobic tails of phospholipid to form strong interactions with the nanomaterial. FIGS. 1A and 1B[23] shows an expected structure of the L-FND, where a lipid layer formed on the surface of FND and any desired functional groups (e.g., biotin, carboxyl groups, etc.) can be added through minor changes of the lipid recipe.

Figure 2C:
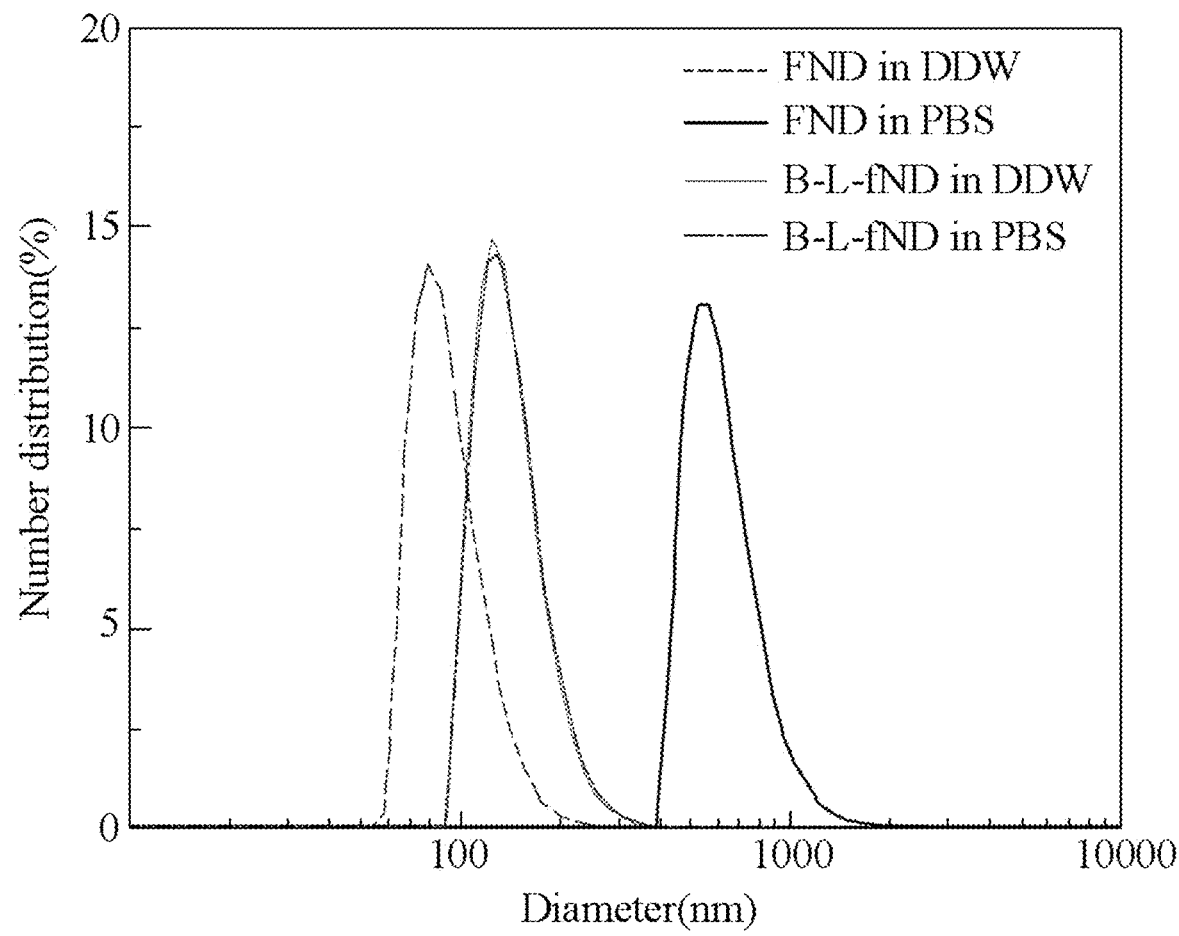
Figure 2D:
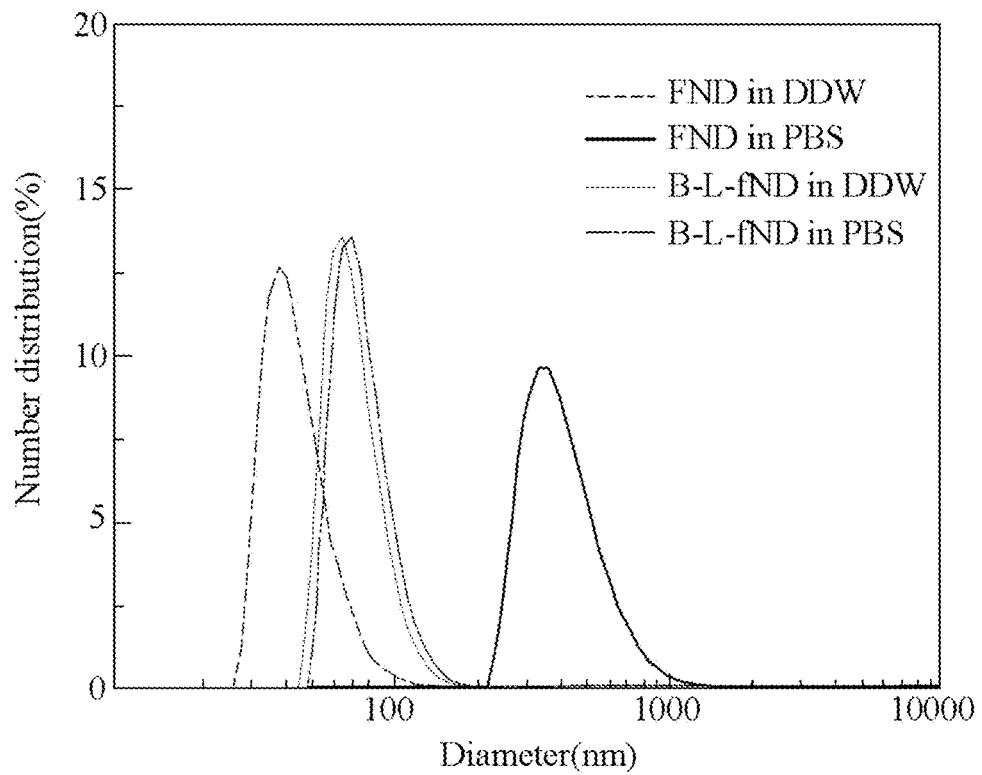
Figure 2E:
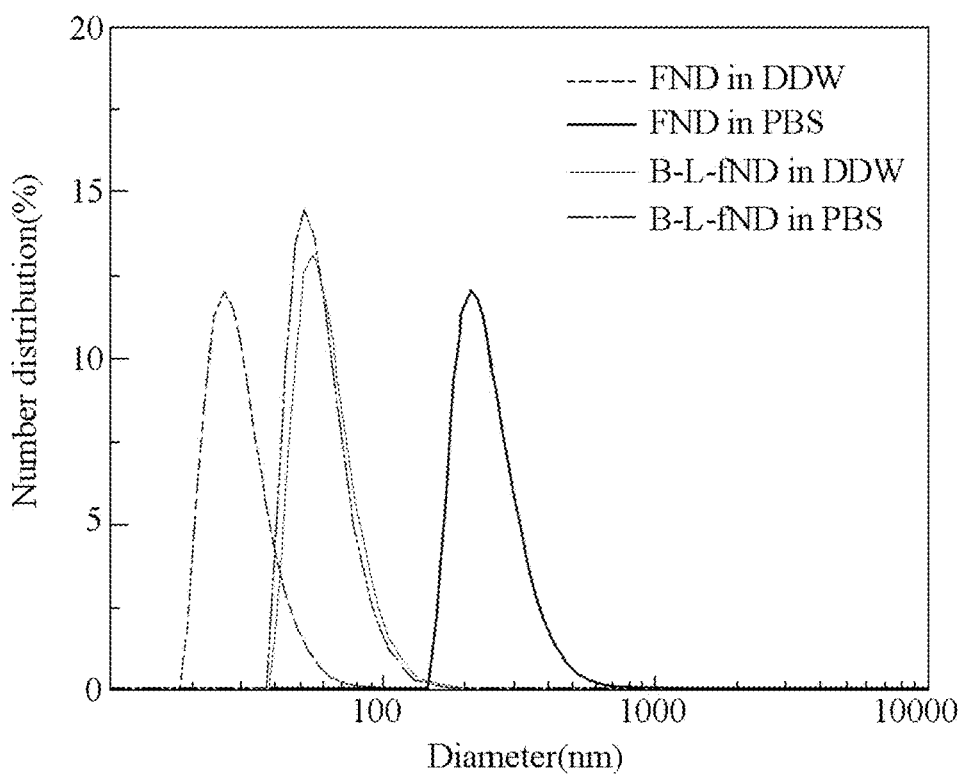

To optimize the lipid/FND ratio for the L-FND preparation, the size was measured by flow cytometry. For air-oxidized FNDs of 100 nm in diameter, the optimal lipid/FND ratio to ensure good dispersibility was found to be 32:1 in weight. Then, it was to examine if the number of washing cycles (i.e. the steps to remove free micelles in the lipid-FND solution) would influence the stability of L-FND in PBS. DLS measurements of L-FND in distilled deionized water (DDW) and PBS indicated that L-FND could still be well dispersed in PBS after 3-6 washes. To functionalize L-FNDs with biotin, 1% of biotinylated PEG2000-DSPE was added into the lipid mixture to form biotinylated L-FND (bL-FND). However, the bL-FNDs easily aggregated in PBS (Table 1). As well documented in literature,[26] the stability of colloidal particles in solution depends on the integration of various forces including van der Waals force, double electric layer force, and steric hindrance force. Hence, the steric hindrance force on the FND surface was raised to address this issue. Indeed, the aggregation problem can be largely solved if the bL-FND contains a higher percentage of PEG2000-DSPE (Table 1). For bL-FNDs containing 9% of PEG2000-DSPE and 1% of biotin-PEG2000-DSPE (10% of PEG2000-DSPE in total), transmission electron microscopy (TEM) imaging revealed a very thin layer of lipid on the particles (FIG. 2A). The size distributions of these bL-FNDs in DDW and PBS are 146±5 nm to 157±3 nm (FIG. 2B), respectively, indicating that the lipid-coated FNDs can be stably dispersed in high ionic strength medium. In contrast, the size distributions of the FNDs without lipid coating increase sharply from 92 nm in DDW to 924 nm in PBS. A similar result was obtained for 50 nm FNDs before coating (45 nm in DDW and 479 nm in PBS) and after coating (60 nm in DDW and 77 nm in PBS) with bL (FIG. 2C).

As shown in FIG. 11, a lipid-coated FND according to another embodiment of the present invention is provided. The lipid-coated FND which is maleimide-modified at its surface and comprises a maleimide-modified lipid (i.e., amphiphilic) capsule and a functional diamond crystal core. In detail, the lipid capsule contains 40% of L-α-phosphatidylcholine (Egg PC), 9% of 1,2-di stearoyl-sn-glycero-3-phosphoethanolamine-N-[methoxy(polyethyleneglycol)-2000 (PEG2000-DSPE), 1% of 1,2-di stearoyl-sn-glycero-3-phosphoethanolamine-N-[maleimide(polyethylene glycol)-2000](PEG2000-DSPE-maleimide) and 50% of cholesterol. The PEG2000-DSPE-maleimide provides a grafting function in the present embodiment. When the maleimide-modified lipid-coated FNDs conjugate with the anti-human CD44 antibodies, they are capable of specifically targeting/labelling the CD44 antigens on the cell surface of HeLa cells (ATCC® CCL-2™). The immunostaining results are shown in FIG. 12.

As shown in FIG. 13, a lipid-coated FND according to yet another embodiment of the present invention is provided. The lipid-coated FND which is DOTAP (1,2-dioleoyl-3-trimethylammonium-propan)-modified at its surface and comprises a DOTAP-modified lipid (i.e., amphiphilic) capsule and a functional diamond crystal core. In detail, the lipid capsule contains 40% or 45% of L-α-phosphatidylcholine (Egg PC), 1% or 5% of 1,2-dioleoyl-3-trimethylammonium-propan (DOTAP) and 50% of cholesterol. The size distributions of the lipid-coated FNDs are shown in the following Table 2. The DOTAP molecules may contribute to elevate the surface potential (ζ-potential) of the lipid-coated FNDs of the present embodiment. As shown in the following Table 3, when the content of the DOTAP in the lipid capsule increases, the surface potential of the lipid-coated FNDs gradually elevated from negative to positive.

TABLE 1

Size distributions of bL-FNDs made of (A) 1% biotin-PEG-DSPE, (B) 0.5% biotin-PEG-DSPE and 4.5% PEG-DSPE, (C) 1% biotin-PEG-lipid and 4% PEG-lipid, (D) 1% biotin-PEG-lipid and 9% PEG-lipid in DDW or PBS.

| | 1% B-PEG | | 0.5% B-PEG 4.5% PEG | | 1% B-PEG 4% PEG | | 1% B-PEG 9% PEG | |
|---|---|---|---|---|---|---|---|---|
| solvent | In H$_2$O | In PBS | In H$_2$O | In PBS | In H$_2$O | In PBS | In H$_2$O | In PBS |
| Size (nm) | 205 ± 9 | 211 ± 57 | 146 ± 7 | 154 ± 9 | 156 ± 12 | 166 ± 26 | 150 | 155 |

TABLE 2

Size distributions of FNDs made of (A) FNDs only, (B) 50% EGG PC and 50% cholesterol, (C) 49% EGG PC, 50% cholesterol, and 1% DOTAP, (D) 45% EGG PC, 50% cholesterol, and 5% DOTAP in DDW and in PBS.

| | FND only | | 50% EGG PC 50% cholesterol solvent | | 49% EGG PC 50% cholesterol 1% DOTAP | | 45% EGG PC 50% cholesterol 5% DOTAP | |
|---|---|---|---|---|---|---|---|---|
| | In H$_2$O | In PBS | In H$_2$O | In PBS | In H$_2$O | In PBS | In H$_2$O | In PBS |
| Size (nm) | 91 | 623 | 111 | 136 | 99 | 205 | 107 | 244 |

TABLE 3

Surface potential (ζ-potential) of the lipid-coated FNDs made of (A) FNDs only, (B) 50% EGG PC and 50% cholesterol, (C) 49% EGG PC, 50% cholesterol, and 1% DOTAP, (D) 45% EGG PC, 50% cholesterol, and 5% DOTAP in DDW.

| | FND only | 50% EGG PC 50% cholesterol | 49% EGG PC 50% cholesterol 1% DOTAP | 45% EGG PC 50% cholesterol 5% DOTAP |
|---|---|---|---|---|
| ζ-potential (mV) In H$_2$O | −43 | −35 | −10 | 8.61 |

As shown in FIG. 14, a lipid-coated FND according to still another embodiment of the present invention is provided. The lipid-coated FND which is stearic-acid-modified at its surface and comprises a steric-acid-modified lipid (i.e., amphiphilic) capsule and a functional diamond crystal core. In detail, the lipid capsule contains steric acid and cholesterol.

As shown in FIG. 15, a lipid-coated FND according to still another embodiment of the present invention is provided. This lipid-coated FND comprises a functional diamond crystal core and a capsule which encapsulates the functional diamond crystal core and is formed with a plurality of amphiphilic fatty acid molecules. As shown in the figure, each fatty acid molecular comprises a hydrophilic head and two lipid tails. Each fatty acid molecule forms a covalent link with nearby (i.e., the neighboring) fatty acid molecule(s). Moreover, each lipid tail also forms a covalent link with its neighboring lipid tail. This lipid-coated FND is a photo-crosslinked lipid-coated FND (FND-PCL). Briefly, such lipid-coated FND may be synthesized as follows. FNDs, 1,2-bis(10,12-tricosadiynoyl)-sn-glycero-3-phosphocholine (diyne PC), and cholesterols were first dissolved in a mixed solution of deionized distilled water (DDW) and tetrahydrofuran (THF). After removal of THF by evaporation, the lipids were automatically arrayed on the surface of FNDs through the Ouzo effect, producing lipid-coated FNDs. The solution was then irradiated with UV at 254 nm to yield FND-PCL. As a result, each lipid tail is cross-linked with its neighboring lipid tail after UV irradiation. The synthesis, characterization, and applications of this photo-crosslinked lipid-coated FND (FND-PCL) may be referenced to Hsieh F-J et. al., "Correlative Light-Electron Microscopy of Lipid-Encapsulated Fluorescent Nanodiamonds for Nanometric Localization of Cell Surface Antigens." (*Anal Chem* 2018 90 (3):1566-1571), and it is hereby incorporated by reference in its entirety.

Experimental Example 2: Immunostaining

In an illustration for the usefulness of bL-FNDs as fluorescent markers, the bL-FNDs were applied to label CD44 antigens on the surface of HeLa cells by sandwich immunostaining (FIG. 16. Briefly, HeLa cells were first fixed with 4% paraformaldehyde. They were then sequentially stained with biotinylated anti-CD44 antibodies, DyLight®488 conjugated neutravidin, and bL-FNDs at a particle concentration of 100 μg/mL for 30 min (FIG. 16). Confocal fluorescence imaging of the cells showed good co-localization of FND and DyLight®488 (B in FIG. 3) on cell membrane, confirming the high specific labeling capability of the particles. The fluorescence images were acquired by laser excitation at 488 nm for DyLight®488 and at 561 nm for FND, and their corresponding fluorescence emission was collected at 500-550 nm and 600-800 nm, respectively. To determine the optimal content of biotin on the FND surface, bL-FNDs with different molar ratios of biotin (i.e., 0%, 0.5% or 1%) were produced to label CD44 antigens on HeLa cells. Flow cytometry (FIGS. 4A-4C) indicated that bL-FNDs containing a higher amount of biotin have higher targeting efficiency but the effect reached a plateau at 1%. Based on the above, the bL-FNDs containing 1% of biotin-PEG2000-DSPE and 9% of PEG2000-DSPE were chosen to use in the following studies.

Figure 5:
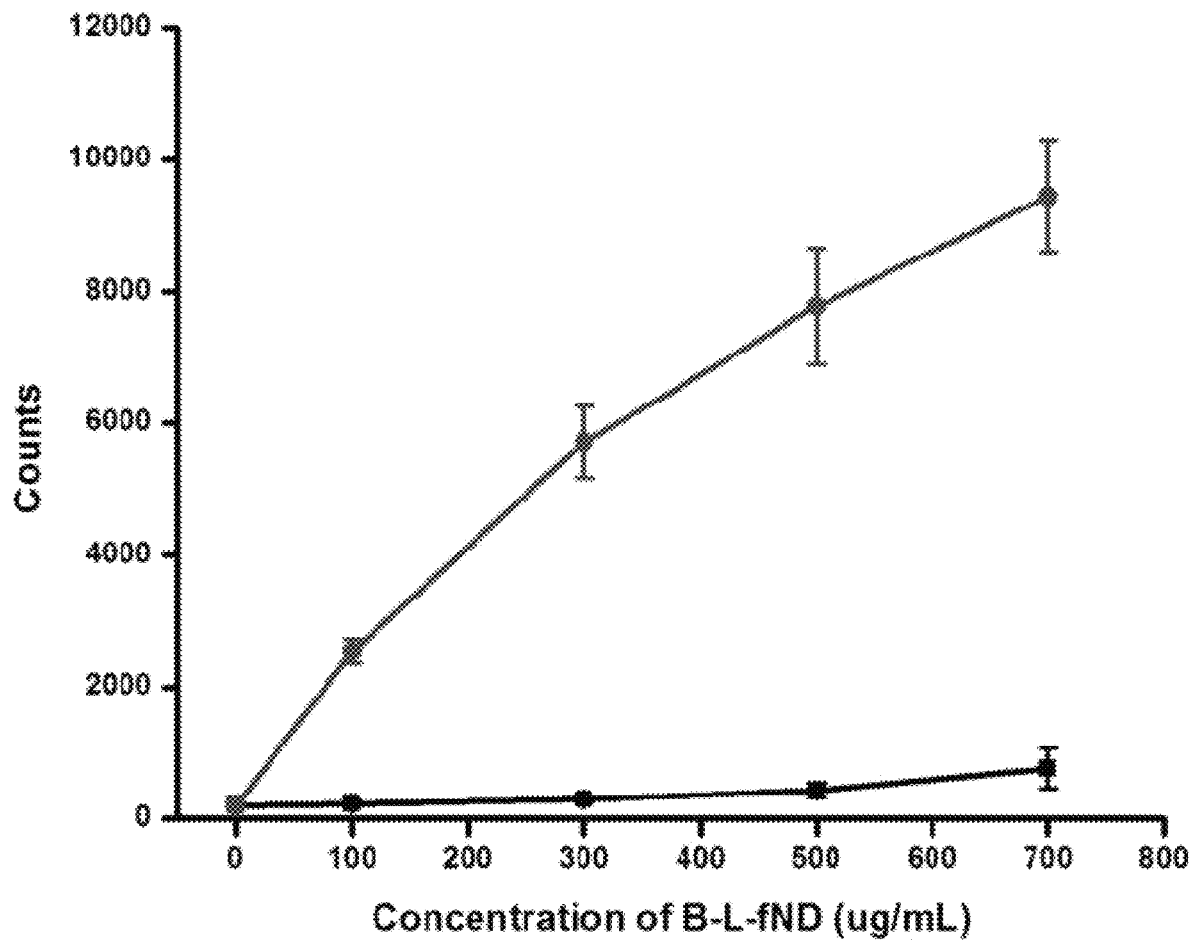
FIG. 5. Flow cytometric analysis of HeLa cells labelled with various concentrations of 100 nm bL-FNDs containing 1% of biotin.

Then, the dose dependence of the labeling was explored by flow cytometry. Non-specific labeling is the major concern to be addressed. As shown in FIG. 5, the amount of FNDs on HeLa surface increased smoothly with the increasing particle concentration up to 700 μg/mL.

Although the higher concentration of bL-FND boosted the fluorescence intensity by a factor of ~4 from 100 to 700 μg/mL, it also substantially levels up the signals due to non-specific labeling. At 700 μg/mL, the non-specific labeling contributed to up to 6% of the total signals. To avoid non-specific labeling of surface CD44, bL-FNDs with a concentration of 100 μg/mL were applied for subsequent nanoscale localization of surface antigens.

Figure 3:
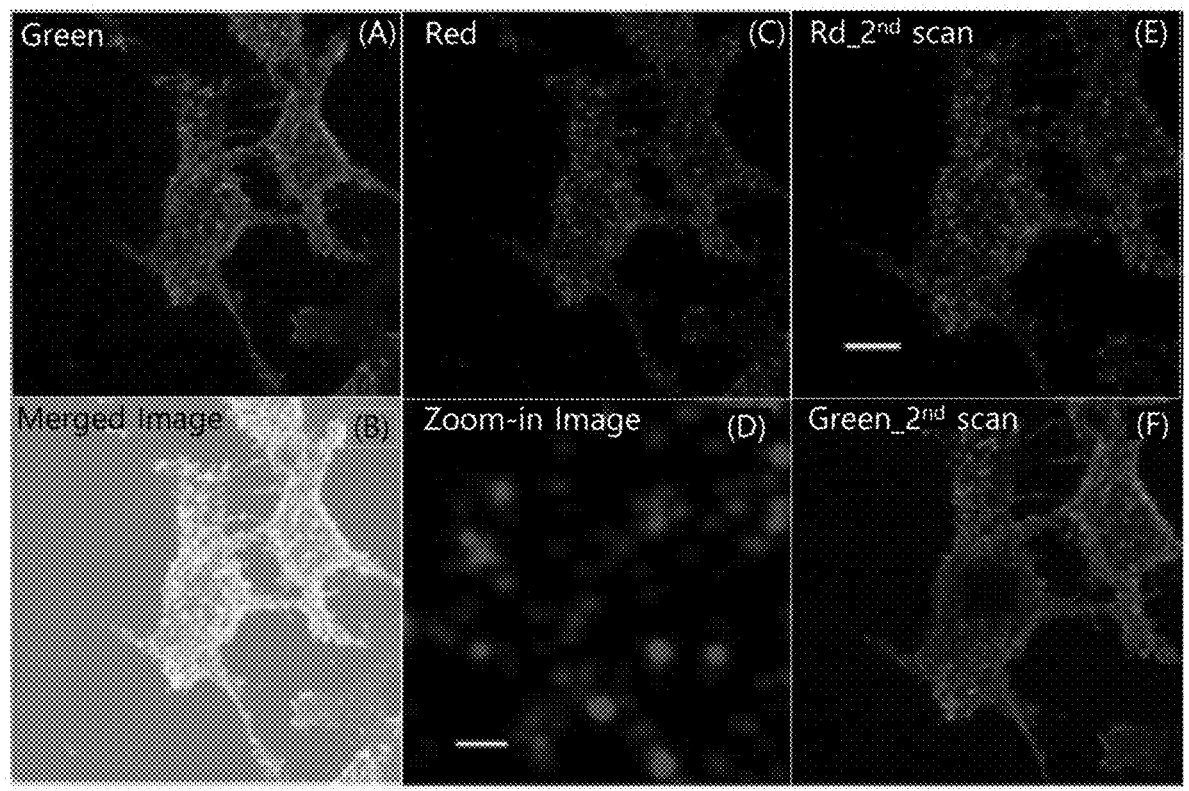
FIG. 3. Bright-field and Z-stacked confocal microscopy images of HeLa cells labelled with 100 nm bL-FNDs containing 1% of DSPE PEG200 biotin. The images of cells labelled with biotin-anti-CD44 antibody, DyLight®488-NA and bL-FND (A-F).
Figure 4A:
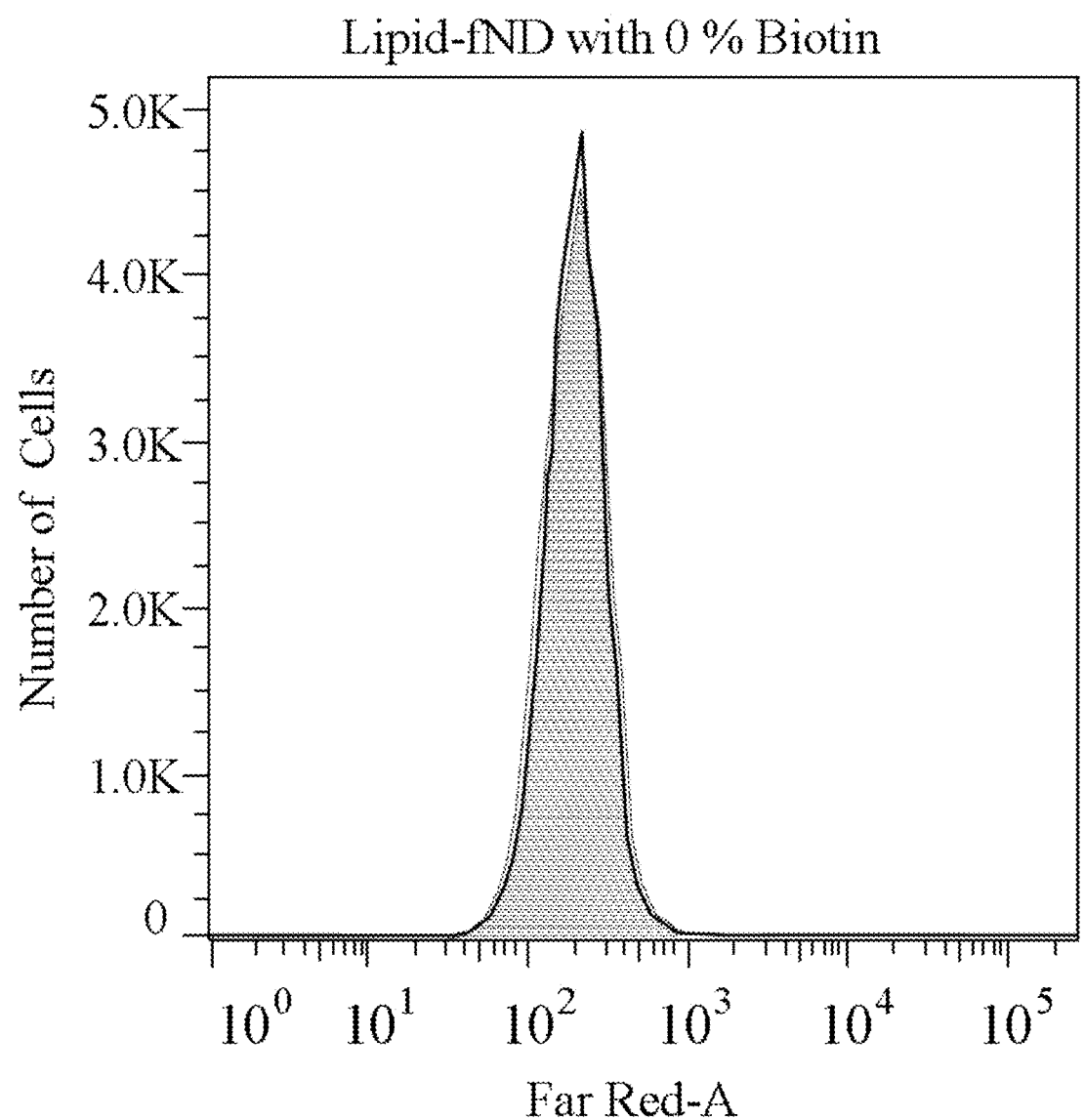
FIGS. 4A-4C. Flow cytometric analysis of HeLa cells labelled with or without 100 nm of bL-FNDs consisting of various molar percentages of biotin. HeLa cells were labelled with bL-FNDs containing 0% (FIG. 4A), 0.5% (FIG. 4B), and 1% (FIG. 4C) of biotin. The blue curves mean cell only, the pink curves represent cells labelled with biotin-anti-CD44 antibody and bL-FND, and the black curves serve as cells labelled with biotin-anti-CD44 antibody, DyLight®488-NA and bL-FND.
Figure 4B:
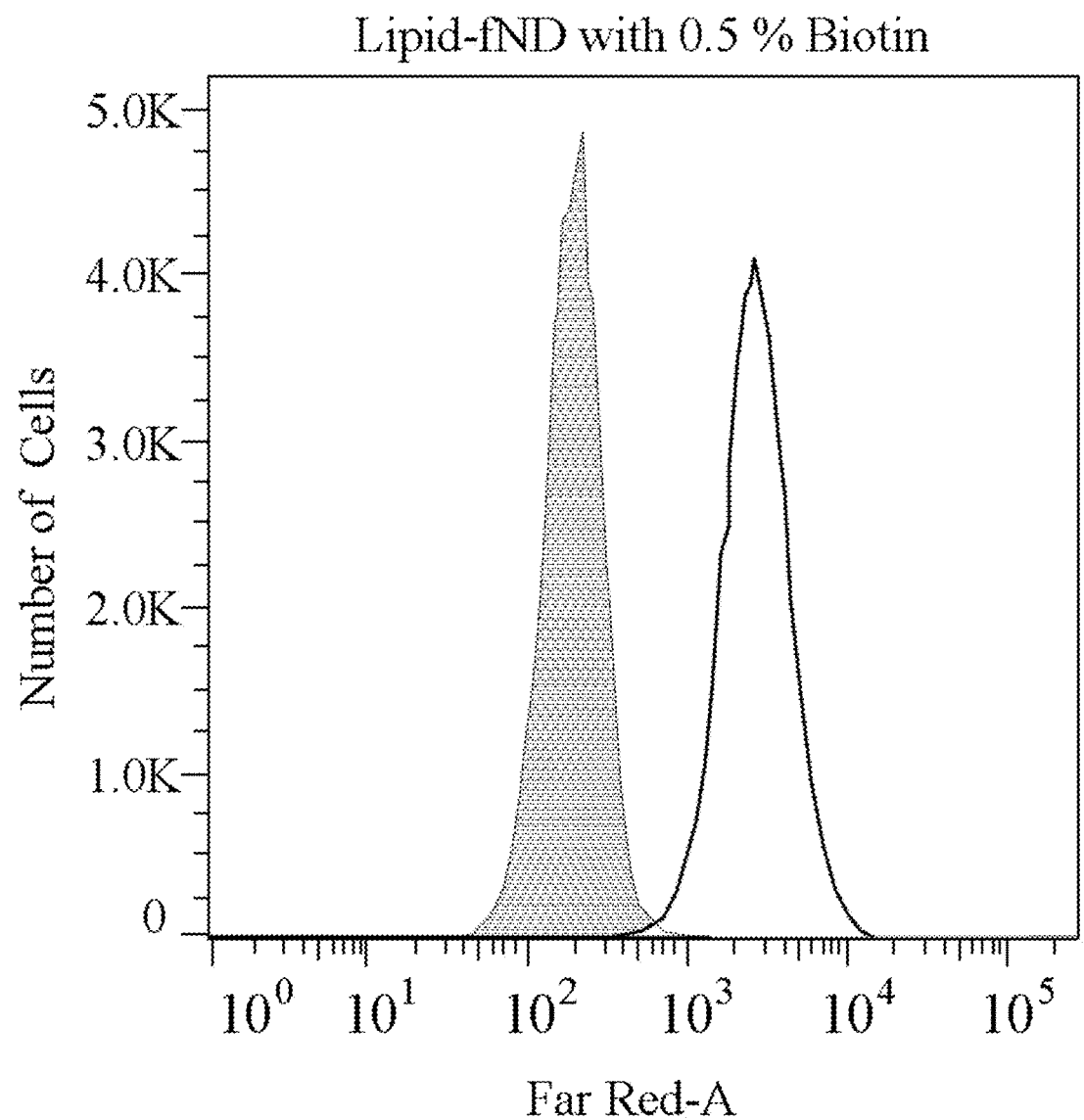
Figure 4C:
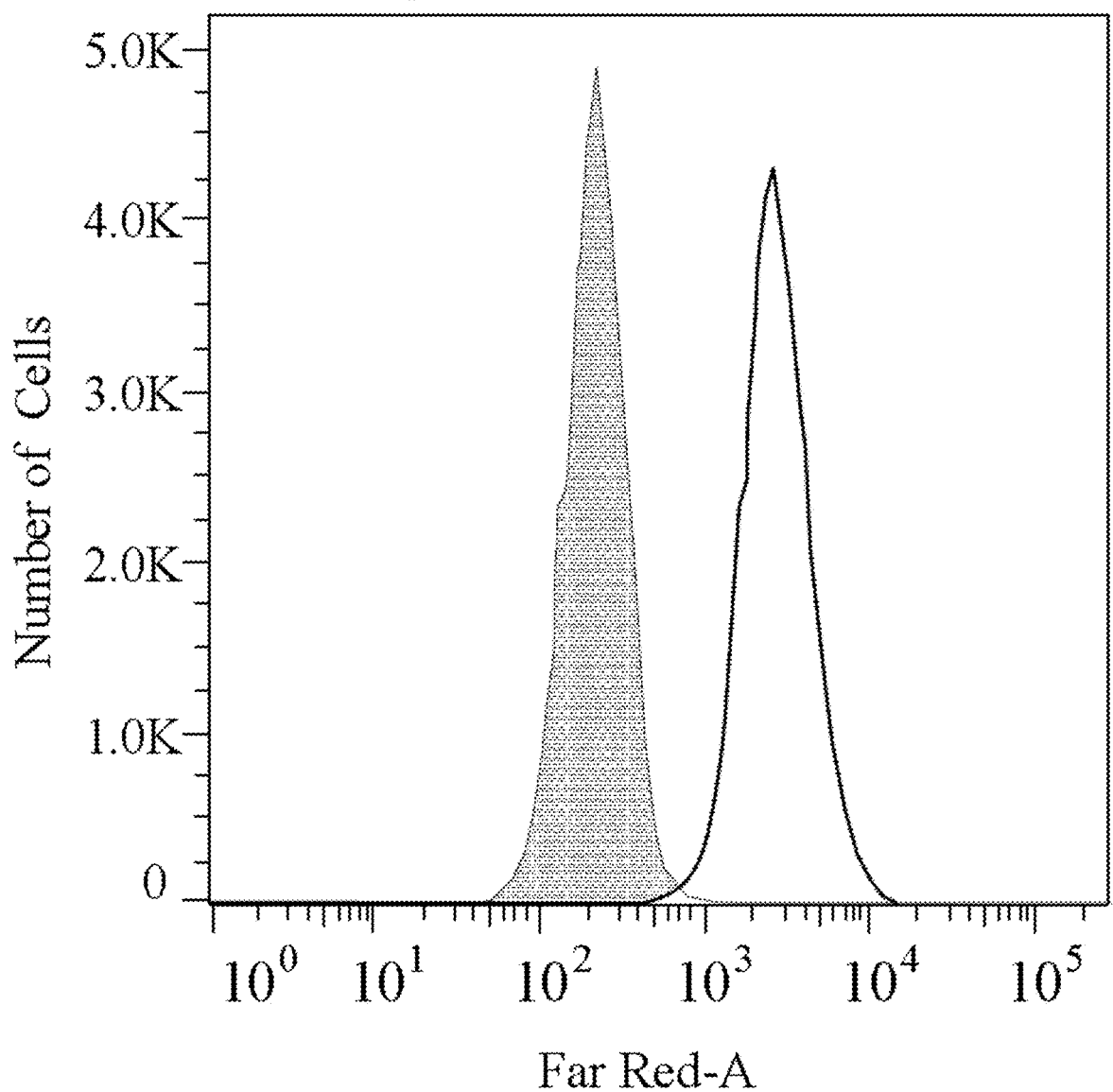

Having confirmed the lack of non-specific labeling at the bL-FND concentration of 100 μg/mL, the images shown in FIG. 3 were expanded to examine the particles individually (D in FIG. 3). Many of the red fluorescence spots have diffraction-limited sizes, suggesting that they are derived from single FND particles. These particles did not photobleach (E in FIG. 3), in stark contrast to that of DyLight®488 (F in FIG. 3), whose fluorescence emission could be barely detected during the 2$^{nd}$ scan of the excitation laser to obtain the images. There is essentially no non-specific bL-FND targeting of CD44 on the HeLa cell surface as shown in the control experiment (FIG. 19).

The ND-based immunostaining technique were have further applied to other cells and compared its performance with that of dye labeling (such as Atto542-biotin). Two types of breast cancer cell lines are used in this study: MCF7 and ASB145-1R. These cells are known to express different levels of CD44 on cell surface.[17] Flow cytometric analysis of HeLa cells labeled with Atto542-biotin (A, C, and E in FIG. 20) or bL-FND (B, D, and F in FIG. 20) showed that both the immunolabeling agents can specifically target CD44 antigens on the cell surface. The 100-nm bL-FND outperformed Atto542-biotin by a significant margin, although they are much larger in size.

Experimental Example 3: Absolute Quantification

Figure 6A:
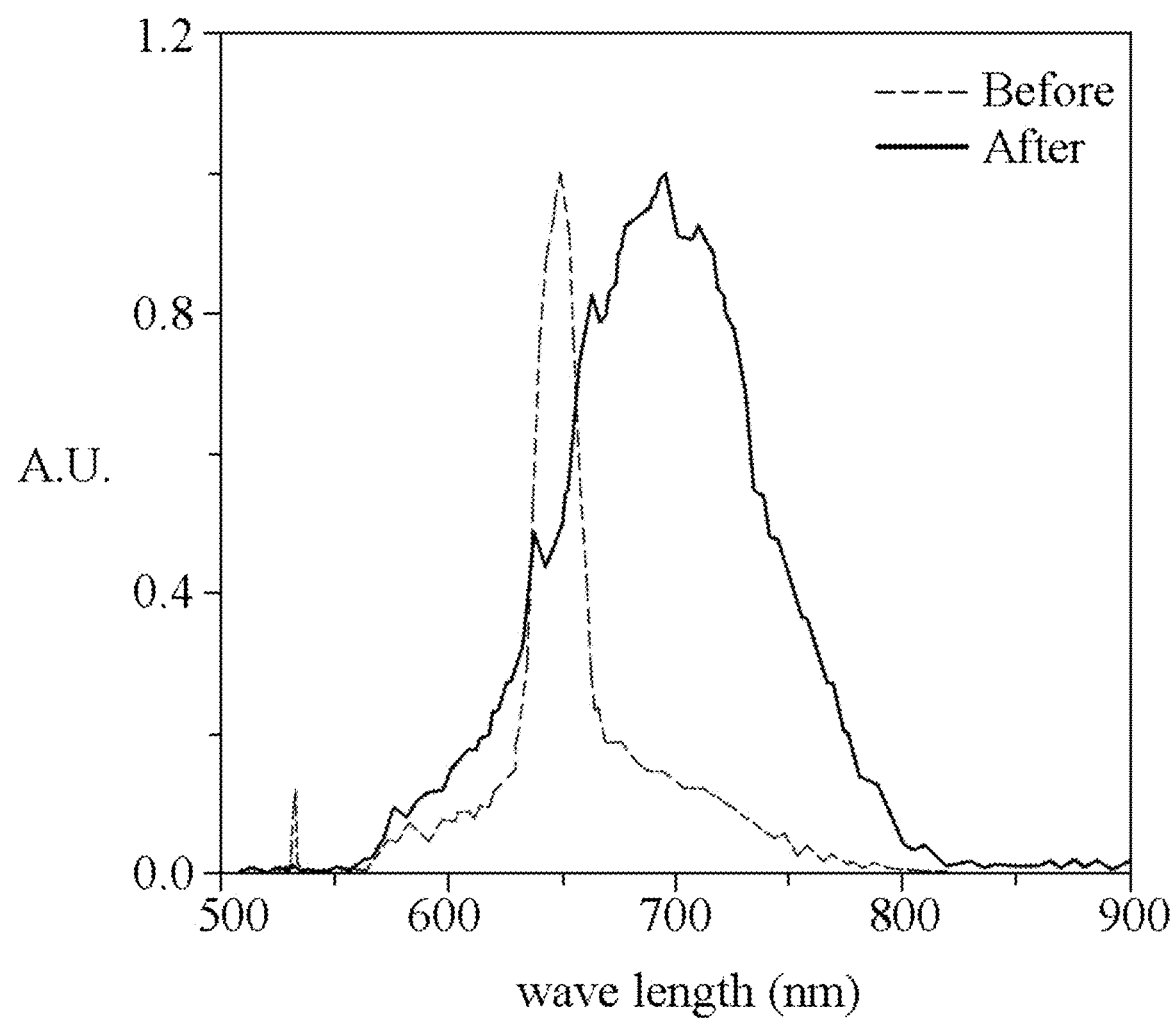
FIGS. 6A-6C.

The observation that the surface antigens were not completely targeted or saturated even at the concentration of 700 μg/mL (FIG. 5) suggested that the number of the particles is too low for labeling. For 100-nm bL-FND, the concentration of 700 μg/mL corresponds to $4 \times 10^{11}$ particles/mL, which is lower than DyLight®488 (1 mM) by more than 6 orders of magnitude. To overcome this limitation but keep the weight concentration the same at 100 μg/mL, the particle size was reduced to be from 100, 50, to 35 nm, which effectively increases the particle number by 1-, 8-, to 24-fold. (FIGS. 6A-6C) Next, absolute quantification of the bL-FNDs on HeLa cell surface was performed by using a magnetically modulated fluorescence technique as described in the previously work for these three types of particles made by the inventors.[28] Briefly, cells labeled with bL-FNDs were sonicated to release the particles from the membrane. The sonicated cell suspension was then measured with a home-built fluorescence spectrometer featuring a magnetic modulation function to eliminate the background fluorescence (FIG. 21). This feature is particularly important when the particle concentration is low, <1 μg/mL, where the Raman peaks of water dominate the spectra (FIG. 6A).[28] The measured total fluorescence intensities were then compared with the calibration curves of the individual samples to obtain the particle numbers.

Figure 6B:
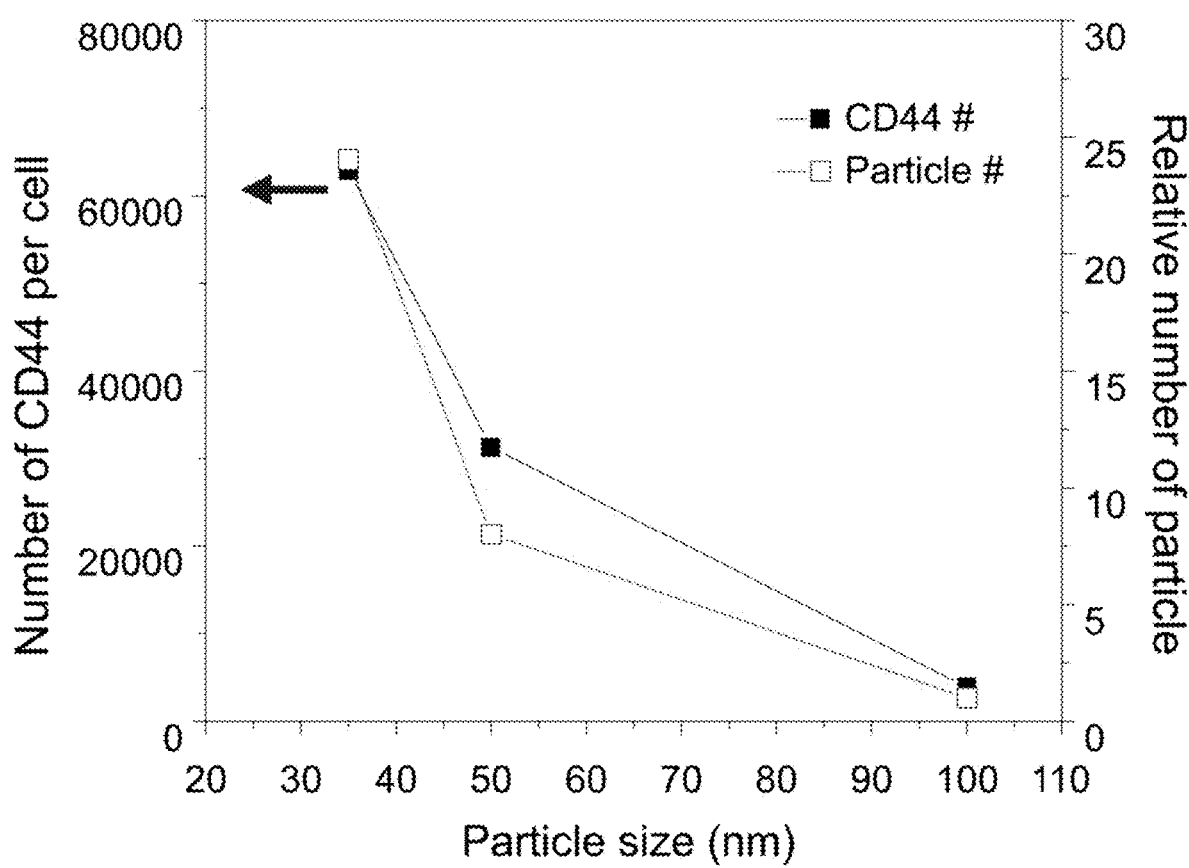
Figure 6C:
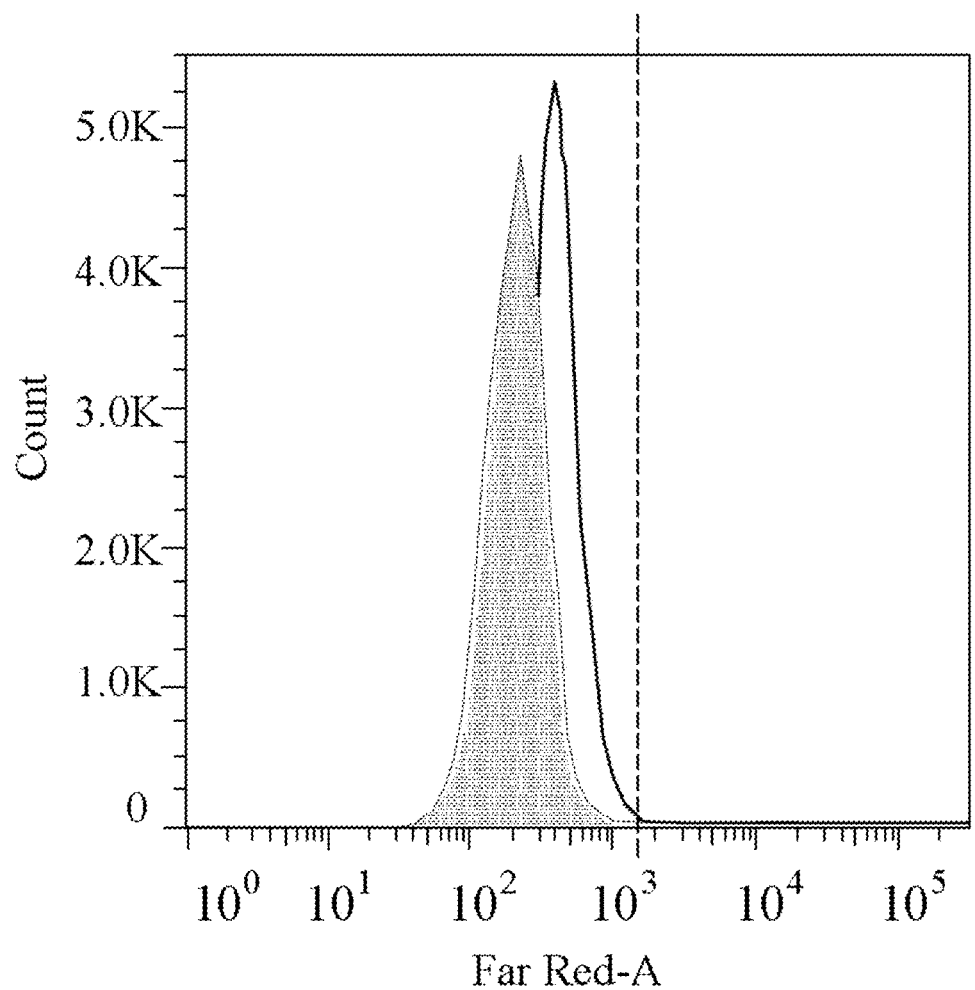

FIG. 6B shows results of the measurements for the three labeling agents. For the 100 nm ones, $5.3 \times 10^3$ bL-FNDs were determined on each HeLa cell surface, which represents only a fraction of CD44 antigens on the cell membrane. Next, the bL-FND made of 50-nm particles was tried. Under the same unit of mass, the amount of lipid used in the encapsulation of FNDs was increased by 2-fold, since the specific surface area of the FND increases linearly with the decreasing particle size. The number of the antigens determined dramatically increases to $3.2 \times 10^4$ and further climbs up to $6.2 \times 10^4$ when 35-nm bL-FNDs were used in the labeling. The trend of the increase agrees satisfactorily with the relative number among the three particles in the cell medium (FIG. 6B), suggesting that the labeling even with 100 nm bL-FNDs is not a diffusion-limited process. With this large amount of antigens on surface, the fluorescence signals could be readily detected by flow cytometry, as shown in FIG. 6C.

To verify the reliability of the absolute quantification method for cell surface antigens with 35-nm bL-FNDs as the biolables, it is crucial to compare the present approach with other methods. For this purpose, the result of this embodiment was compared with that of the QuantiBRITE™-PE method developed to determine the number of R-phycoerythrin (R-PE)-conjugated antibodies bound to a cell by flow cytometer using amino-functionalized poly(methyl methacrylate) (PMMA) beads with known numbers of attached R-PE molecules.[29,30] R-PE was chosen for the quantitation fluorochrome because it lacks self-quenching and can form well-defined antibody conjugates. Similar to the FND quantification, the antibody-binding capacity (ABC) of the cells can be determined by comparison of the flow cytometry signals against a calibration curve prepared with the R-PE-conjugated PMMA beads (6 μm diameter). With this commercially available kit, a value of $ABC=6.9 \times 10^4$ was determined, which matches closely with the measurement of $ABC=6.9 \times 10^4$ using the 35-nm bL-FNDs. The agreement suggests that our bL-FND nanobeads are useful as tool to determine the ABC of fixed cells without the need to use R-PE. Most of the epitopes on the cell surface are accessible to the antibodies attached to the nanobeads.

Experimental Example 4: Correlative Light Electron Microscopy (CLEM)

Conventionally, the detection and localization of cell surface molecules are performed by single-particle imaging using fluorescent protein molecules such as R-PE.[31,32] However, photobleaching of the molecules disallows their tracking over a long period of time. CLEM is a technique recently developed to allow the analysis of the same specimen with both light microscopy (LM) and electron microscopy (EM). Differing from cathode luminescence, the images are acquired with two vastly different instruments and therefore localization of the same objects at the micrometer scale is critically important. As a result, colloidal gold particles (e.g. 15 nm in diameter) must be added to the grids (and section) to serve as fiducial markers for the alignment of the specimens. In addition, to preserve the morphology of the specimen, LM had better be performed after embedding of the samples for EM. However, the post embedding approach requires direct LM imaging of the sections after heavy metal staining on the TEM grids. Although there are some successful cases with fluorescent proteins[33] and chemical tags,[34] the studies remain a challenge.

Figure 7:
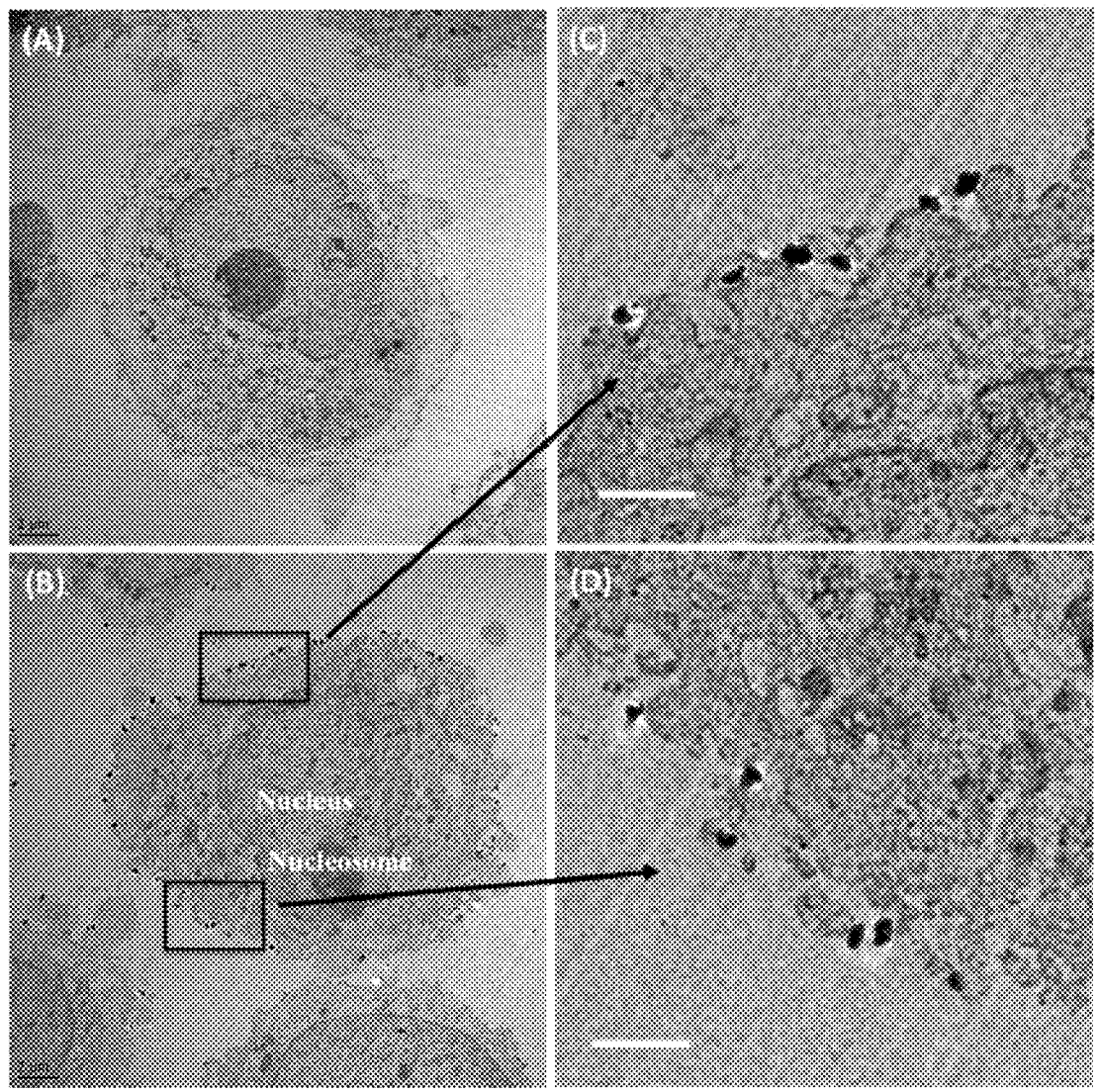
FIG. 7. TEM images of HeLa cells (A) or HeLa cells labelled with biotin-antiCD44 antibody, neutravidin, and then bL-FNDs (B-D).
Figure 8:
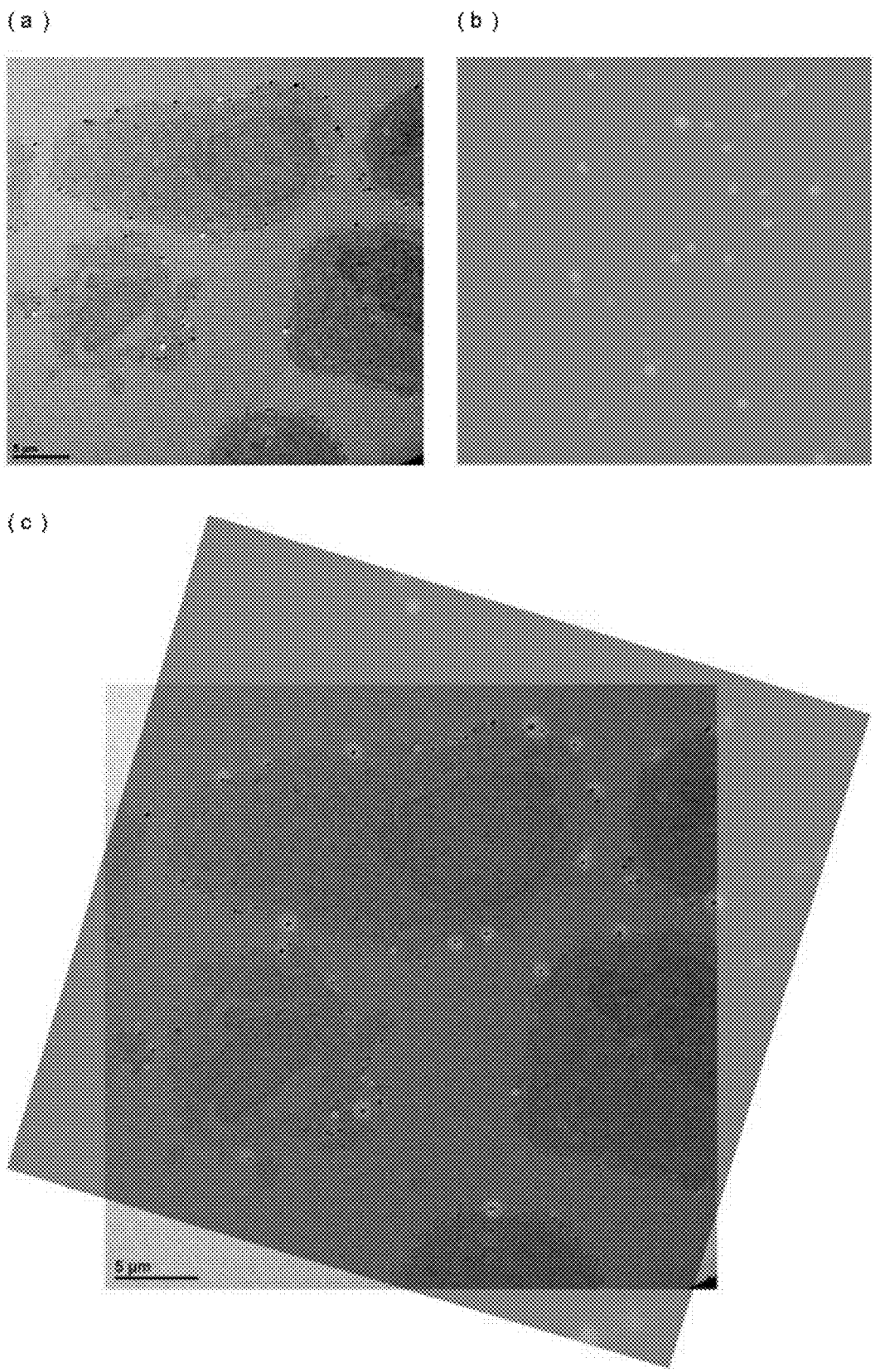
FIG. 8. (a) TEM, (b) fluorescence, and (c) CLEM images of HeLa cells labelled with biotinanti-CD44 antibody, neutravidin, and then bL-FNDs. TEM images of suspended HeLa cells labeled with biotin-anti-CD44 antibody, neutravidin, and then bL-FND. The electron energy used to obtain the TEM images is 120 kV. Scale bars: 5 μm (a, c).
Figure 9:
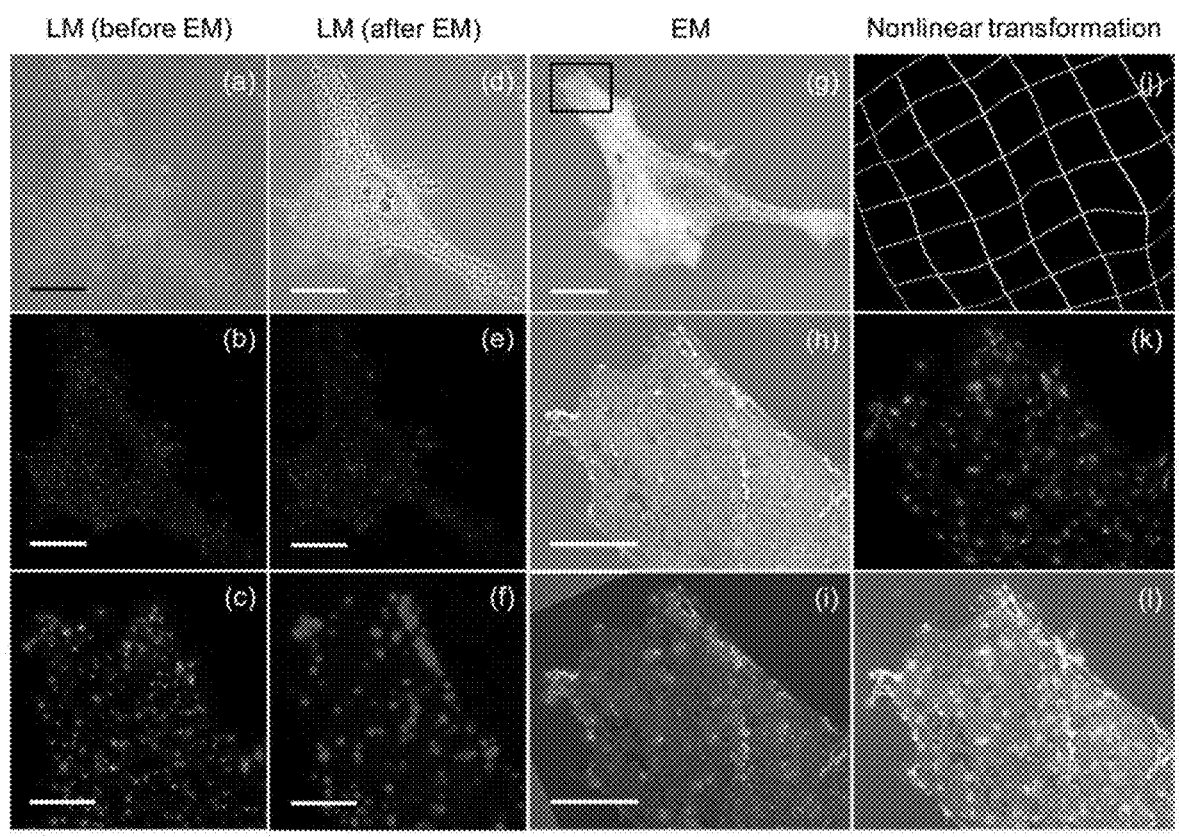
FIG. 9. (a-f) Bright-field and Z-stacked confocal microscopy images of a HeLa cell first labeled for MICA/MICB antigens with the Alexa Fluor 488 dye and then for CD44 antigens with bL-FND by immunostaining before (a-c) and after (d-f) SEM imaging. (c, f) Zoom-in fluorescence images of the cell before (c) and after (f) SEM imaging. Note the significant morphological change after SEM imaging and the disappearance of green emission in (f). (g-i) SEM images of the MICA/MICB- and CD44-labeled HeLa cell. (h)

FND is a nanomaterial having both the high fluorescence capability and a dense carbon core that can be visualized by EM. Moreover, the detection of the nanomaterial by fluorescence imaging is compatible with the post-embedding technique, which involves staining of the samples with heavy metals such as uranyl acetate for structural preservation in EM. The high compatibility is derived from the fact that the fluorescent centers of FNDs are buried deep inside the diamond matrixes and their properties are insensitive to environmental changes. FIG. 7 displays TEM images of HeLa cells without labelling and HeLa cells labelled with biotin-anti-CD44 antibody, neutravidin, and then bL-FNDs. The 100-nm FND particles in the thin-sectioned, resin-embedded specimens could be individually identified with resolution of better than 10 nm on the cell surface. More importantly, the EM image (FIG. 8A) and the LM image (FIG. 8B) can be readily superimposed with each other using FNDs as the fiducials (FIG. 8C). Up to 30 particles show excellent registration of the two images when the fluorescence image was tilted by 17°. An enlarged view of the fluorescence spots was also shown and they were fitted with point spread functions (data not shown). Thanks to the high brightness and perfect photostability of 100-nm bL-FNDs, the positions of the CD44 antigens can be localized with an accuracy of better than 50 nm (data not shown). The combined LM and EM analysis enables localization of the CD44 antigens on HeLa cell surface with unprecedented accuracy. FIG. 9 is another CLEM example done by imposing SEM and LM images. Owing to the strong structure of FNDs, FNDs can be used as fiducial markers to label the positions of antigens on cell surface under strict surrounding. By comparison, conventional dyes (i.e., Alexa fluors) is bleached after sample preparation and EM observation. FIG.

10 shows that the possibility of using FND to localize the position of vaccinia virus on HeLa cell surface.

As shown in above, the present disclosure has demonstrated that FND is a biocompatible nanoprobe with unique magneto-optical properties, including exceptionally high photostability, magnetically modulable fluorescence intensity, and longlived fluorescence lifetime. These properties together make it possible to achieve high-quality and background-free imaging and localization of cellular components with nanoscale resolution if the nanoparticles are endowed with specific targeting abilities. This work demonstrates that FNDs surface-oxidized in air can be facilely encapsulated in lipids by utilizing the Ouzo effect, and these lipid-encapsulated FNDs are useful as specific cell targeting agents after proper conjugation of the lipid layers with bioactive molecules such as biotin. These lipid-encapsulated FNDs have been applied for absolute quantification and nanoscale localization of CD44 antigens on HeLa cell membrane with CLEM to prove the principle. The method is general and applicable to other biomolecules since a variety of lipid derivatives are now commercially available and they all serve well the purpose after minor modification of the protocols illustrated in this work.

It will be appreciated by those skilled in the art of the changes could be made to the embodiments described above without departing from the broad invention concept thereof. It is understood, therefore, that this invention is not limited to the particular embodiments disclosed, but it is intended to cover modification within the spirit and scope of the present invention as defined by the appended claims.

REFERENCES

1. L. Dean, In: Blood Groups and Red Cell Antigens [Internet]. Bethesda (Md.): National Center for Biotechnology Information (US). 2005, Chap. 2.
2. P. J. Delves, CD Antigens. In: eLS. John Wiley & Sons, Chichester. 2016, p. 1.
3. E. V. Lourenco, M. C. Roque-Barreira, *Methods Mol Biol.* 2010, 588, 301.
4. H. Kim, S. Tsuruta, H. Arakawa, T. Osada, A. Ikai, *Ultramicroscopy* 2004, 100, 203.
5. R. de la Rica, M. M. Stevens, *Nat Nanotechnol.* 2012, 7, 821.
6. D. Tang, Y. Cui, G. Chen, *Analyst* 2013, 138, 981.
7. S.-J. Yu, M.-W. Kang, H.-C. Chang, K.-M. Chen, Y.-C. Yu, *J. Am. Chem. Soc.* 2005, 127, 17604.
8. W. W.-W. Hsiao, Y. Y. Hui, P.-C. Tsai, H.-C. Chang, *Acc. Chem. Res.* 2016, 49, 400.
9. Y. Kuo, T.-Y. Hsu, Y.-C. Wu, J.-H. Hsu, H.-C. Chang, *Proc. SPIE* 2013, 8635, 863503.
10. Y. Kuo, T.-Y. Hsu, Y.-C. Wu, H.-C. Chang, *Biomaterials* 2013, 34, 8352.
11. T.-J. Wu, Y.-K. Tzeng, W.-W. Chang, C.-A. Cheng, Y. Kuo, C.-H. Chien, H.-C. Chang, J. Yu, *Nat. Nanotechnol.* 2013, 8, 682.
12. S. K. Sarkar, A. Bumb, X. Wu, K. A. Sochacki, P. Kellman, M. W. Brechbiel, K. C. Neuman, *Biomed. Opt. Express* 2014, 5, 1190.
13. I. Rehor, H. Mackova, S. K. Filippov, J. Kucka, V. Proks, J. Slegerova, S. Turner, G. Van Tendeloo, M. Ledvina, M. Hruby, P. Cigler, *Chempluschem* 2014, 79, 21.
14. J. Slegerova, M. Hajek, I. Rehor, F. Sedlak, J. Stursa, M. Hruby, P. Cigler, *Nanoscale* 2015, 7, 415.
15. S. Sotoma, R. Igarashi, J. Iimura, Y. Kumiya, H. Tochio, Y. Harada, M. Shirakawa, *Chem. Lett.* 2015, 44, 354.
16. S. Sotoma, J. Iimura, R. Igarashi, K. M. Hirosawa, H. Ohnishi, S. Mizukami, K. Kikuchi, T. K. Fujiwara, M. Shirakawa, H. Tochio, *Nanomaterials* 2016, 6, 56.
17. B.-M. Chang, H.-H. Lin, L.-J. Su, W.-D. Lin, R.-J. Lin, Y.-K. Tzeng, R. T. Lee, Y. C. Lee, A. L. Yu, H.-C. Chang, *Adv. Funct. Mater.* 2013, 23, 5737.
18. L. Moore, E. K. H. Chow, E. Osawa, J. M. Bishop, D. Ho, *Adv. Mater.* 2013, 25, 3532.
19. S. A. Vitale, J. L. Katz, *Langmuir* 2003, 19, 4105.
20. M. Beck-Broichsitter, J. Nicolas, P. Couvreur, *Nanoscale* 2015, 7, 9215.
21. J. Nicolas, *Chem. Mater.* 2016, 28, 1591.
22. S.-J. Chiu, C.-Y. Lin, H.-C. Chou, T.-M. Hu, *Langmuir* 2016, 32, 211.
23. Hsieh F-J, Chen Y-W, Huang Y-K, Lee H-M, Lin C-H, Chang H-C, Correlative Light-Electron Microscopy of Lipid-Encapsulated Fluorescent Nanodiamonds for Nanometric Localization of Cell Surface Antigens. Anal Chem 2018 90 (3):1566-1571. doi:10.1021/acs.analchem.7b04549
24. N. Grimaldi, F. Andrade, N. Segovia, L. Ferrer-Tasies, S. Sala, J. Veciana, N. Ventosa, *Chem. Soc. Rev.* 2016, xxx.
25. V. N. Mochalin, O. Shenderova, D. Ho, Y. Gogotsi, *Nat. Nanotechnol.* 2012, 7, 11.
26. E. J. W. Verwey, J. T. G. Overbeek, *Theory of the Stability of Lyophobic Colloids*. Dover, 1999.
27. Sotoma S, Hsieh F-J, Chen Y-W, Tsai P-C, Chang H-C, Highly stable lipid-encapsulation of fluorescent nanodiamonds for bioimaging applications. Chem Commun 2018 54 (8):1000-1003. doi:10.1039/C7CC08496J
28. Su L-J, Wu M-S, Hui Y Y, Chang B-M, Pan L, Hsu P-C, Chen Y-T, Ho H-N, Huang Y-H, Ling T-Y, Hsu H-H, Chang H-C (2017) Fluorescent nanodiamonds enable quantitative tracking of human mesenchymal stem cells in miniature pigs. Sci Rep-Uk 7:45607. doi:10.1038/srep45607
29. K. A. Davis, B. Abrams, S. B. Iyer, R. A. Hoffman, J. E. Bishop, Cytometry 1998, 33, 197.
30. K. K. Pannu, E. T. Joe, S. B. Iyer, Cytometry 2001, 45, 250.
31. K. M. Wilson, I. E. Morrison, P. R. Smith, N. Fernandez, R. J. Cherry, J. Cell Sci. 1996, 109 (Pt 8), 2101.
32. I. E. Morrison, I. Karakikes, R. E. Barber, N. Fernandez, R. J. Cherry, Biophys. J. 2003, 85, 4110.
33. E. Johnson, E. Seiradake, E. Y. Jones, I. Davis, K. Grünewald, R. Kaufmann, Sci. Rep. 2015, 5, 9583.
34. M. Perkovic, M. Kunz, U. Endesfelder, S. Bunse, C. Wigge, Z. Yu, V. V. Hodirnau, M. P. Scheffer, A. Seybert, S. Malkusch, E. M. Schuman, M. Heilemann, A. S. Frangakis, J. Struct. Biol. 2014, 186, 205.

What is claimed is:

1. A nanodiamond particle complex, comprising:
   an amphiphilic capsule which comprises a plurality of fatty acid molecules forming a partial single-layered and partial bi-layered micelle structure; and
   a nanodiamond particle encapsulated in said amphiphilic capsule, wherein the nanodiamond particle has at least one nitrogen-vacancy center,
   wherein the nanodiamond particle complex is prepared by utilizing Ouzo effect.

2. The nanodiamond particle complex according to claim 1, wherein at least one of the fatty acid molecules is modified with a functional group which is configured to graft a recognizing molecule, and said recognizing molecule is configured to be able to specifically recognize an antigen of a biological sample.

3. The nanodiamond particle complex according to claim 2, wherein said functional group is selected from the group consisting of a hydroxyl group, carboxyl group, a biotin moiety, a cyanuric chloride modified group, a thiol group, a maleimide group, an alkyne, an azide group, an antibody, a halo ligand and a combination thereof.

4. The nanodiamond particle complex according to claim 1, wherein said fatty acid molecules are selected from the group consisting of a saturated fatty acid, an unsaturated fatty acid, a phospholipid, a glycol, a cholesterol, and a combination thereof.

5. The nanodiamond particle complex according to claim 4, wherein the phospholipid is selected from the group consisting of phosphatidylcholine, phosphatidylethanolamine, Phosphatidylglycerol, Lyso Lipids, Phosphatidic acid, Sphingolipids, Phosphatidylserine, 1,2-bis(10,12-tricosadiynoyl)-sn-glycero-3-phosphocholine,1-palmitoyl-2-(10,12-tricosadiynoyl)-sn-glycero-3-phosphoethanolamine, 1-palmitoyl-2-(10,12-tricosadiynoyl)-sn-glycero-3-phosphocholine, 1-palmitoyl-2-(10,12-tricosadiynoyl)-sn-glycero-3-phosphoethanolamine, and a combination thereof.

6. The nanodiamond particle complex according to claim 1, wherein the amphiphilic capsule further comprises PEGylated 1,2-distearoyl-sn-glycero-3-phosphoethanolamines (DSPEs) or 10,12-Tricosadiynoic acid, and a part of said PEGylated 1,2-distearoyl-sn-glycero-3-phosphoethanolamines (DSPEs) or a part of said 10,12-Tricosadiynoic acid further comprises a functional group, and the functional group is selected from the group consisting of a hydroxyl group, carboxyl group, a biotin moiety, a cyanuric chloride modified group, a thiol group, a maleimide group, an alkyne, an azide group, an antibody, a halo ligand and a combination thereof.

7. The nanodiamond particle complex according to claim 6, wherein the PEGylated 1,2-distearoyl-sn-glycero-3-phosphoethanolamines are PEG2000-DSPEs and the content ratio between the biotin-labeled PEG2000-DSPEs (biotin-PEG2000-DSPEs) and PEG2000-DSPEs not labeled with biotins (PEG2000-DSPEs) ranges from 1:0.001 to 1:10.

8. The nanodiamond particle complex according to claim 1, wherein the size of the composition of nanodiamond particle complex distributes from 1 nm to 1 mm in diameter.

9. A reagent kit for targeting a biological sample, comprising:
the nanodiamond particle complex according to claim 1, which is configured to be able to specifically recognize an antigen of the biological sample.

10. The reagent kit according to claim 9, further comprising:
a recognizing molecule which is configured to be able to specifically recognize the antigen of the biological sample; and
a grafting molecule which is configured to be able to bind with said recognizing molecule and said nanodiamond particle complex.

11. The reagent kit according to claim 10, wherein the concentration of the nanodiamond particle complex is 0.01 µg/mL to 2000 µg/mL.

12. A method for targeting a biological sample, comprising following steps of:
treating the biological sample with the nanodiamond particle complex according to claim 1 which is configured to be able to be able to specifically recognize an antigen of said biological sample.

13. The method according to claim 12, further comprising a step of observing the biological sample treated with the nanodiamond particle complex observed with light microscopy, electron microscopy or correlative light-electron microscopy.

14. The method according to claim 12, further comprising steps of:
sequentially treating the biological sample with a first reagent comprising a recognizing molecule which is configured to be able to specifically recognize an antigen of said biological sample, a second reagent comprising a grafting molecule which is configured to be able to bind with said recognizing molecule, and then performing the step of treating the biological sample with the nanodiamond particle complex.

15. A method to quantify a concentration of the nanodiamond particle complex according to claim 1 in a sample, comprising:
providing the sample to be tested;
applying the nanodiamond particle complex to the sample; and
measuring a fluorescent signal emitted by the nanodiamond particle complex so as to determine the concentration of the nanodiamond particle complex in the sample.

16. The method according to claim 15, the fluorescent signal of the nanodiamond particle complex is measured with a magnetic field.

17. A method for imaging a sample, comprising:
labelling a sample with a nanodiamond particle complex according to claim 1;
irradiating the labelled sample with an exciting energy; and
generating an image of at least a portion of the sample based on a signal collected from the excited sample.

18. The method of claim 17, wherein the exciting energy is electron, light, microwave, radio waves, infrared, X rays, gamma rays, cosmic rays or a combination thereof.

19. A nanodiamond particle complex, comprising:
an amphiphilic capsule which comprises a plurality of fatty acid molecules forming a partial single-layered and partial bi-layered micelle structure; and
a nanodiamond particle encapsulated in said amphiphilic capsule, wherein the nanodiamond particle has at least one nitrogen-vacancy center,
wherein the nanodiamond particle complex is prepared by utilizing Ouzo effect,
wherein the amphiphilic capsule further comprises PEGylated 1,2-distearoyl-sn-glycero-3-phosphoethanolamines (DSPEs) or 10,12-Tricosadiynoic acid, and a part of said PEGylated 1,2-distearoyl-sn-glycero-3-phosphoethanolamines (DSPEs) or a part of said 10,12-Tricosadiynoic acid further comprises a functional group, and the functional group is selected from the group consisting of a hydroxyl group, carboxyl group, a biotin moiety, a cyanuric chloride modified group, a thiol group, a maleimide group, an alkyne, an azide group, an antibody, a halo ligand and a combination thereof, wherein the PEGylated 1,2-distearoyl-sn-glycero-3-phosphoethanolamines are PEG2000-DSPEs and the content ratio between the biotin-labeled PEG2000-DSPEs (biotin-PEG2000-DSPEs) and PEG2000-DSPEs not labeled with biotins (PEG2000-DSPEs) is 1:9.

* * * * *